(12) United States Patent
Van Antwerp et al.

(10) Patent No.: US 12,295,749 B2
(45) Date of Patent: May 13, 2025

(54) DERMAL SENSOR FOR DETERMINING ANALYTE CONCENTRATIONS

(71) Applicant: LAXMI THERAPEUTIC DEVICES, INC., Goleta, CA (US)

(72) Inventors: William Peter Van Antwerp, Santa Clarita, CA (US); Roshanne Malekmadani, Goleta, CA (US); Matthew Yavorsky, Granada Hills, CA (US); Thomas Metzmaker, Goleta, CA (US); Michael Larkin, Santa Barbara, CA (US)

(73) Assignee: LAXMI THERAPEUTIC DEVICES, INC., Goleta, CA (US)

( * ) Notice: Subject to any disclaimer, the term of this patent is extended or adjusted under 35 U.S.C. 154(b) by 0 days.

(21) Appl. No.: 18/069,715

(22) Filed: Dec. 21, 2022

(65) Prior Publication Data
US 2024/0206814 A1    Jun. 27, 2024

(51) Int. Cl.
*A61B 5/00*    (2006.01)
*A61B 5/145*   (2006.01)

(52) U.S. Cl.
CPC ........ *A61B 5/6839* (2013.01); *A61B 5/14503* (2013.01); *A61B 5/1451* (2013.01); *A61B 5/14532* (2013.01)

(58) Field of Classification Search
None
See application file for complete search history.

(56) References Cited

U.S. PATENT DOCUMENTS

| | | | | |
|---|---|---|---|---|
| 6,091,975 | A * | 7/2000 | Daddona | A61B 5/14865 600/347 |
| 11,298,058 | B2 * | 4/2022 | Stafford | A61B 5/14532 |
| 2019/0117256 | A1 | 4/2019 | Jäger | |
| 2019/0320902 | A1 | 10/2019 | Brister et al. | |
| 2021/0236028 | A1 * | 8/2021 | Mccanless | A61B 5/14503 |
| 2022/0007978 | A1 * | 1/2022 | Oja | A61B 5/14865 |

OTHER PUBLICATIONS

International Search Report and Written Opinion for Application No. PCT/US23/85196, mailed May 23, 2024, 17 pages.

\* cited by examiner

*Primary Examiner* — Michael R Bloch
(74) *Attorney, Agent, or Firm* — Womble Bond Dickinson (US) LLP

(57) ABSTRACT

A monitor for determining analyte concentrations in vivo, includes a housing configured to adhere to the skin of a subject, an elongate sensor body configured to extend from the housing into the skin of the subject, an analyte sensing region positioned on the sensor body such that the analyte sensing region is configured to be held in the dermis of the skin of the subject, and at least one engagement surface configured to facilitate increased anchoring of the sensor body in the skin of the subject.

17 Claims, 22 Drawing Sheets

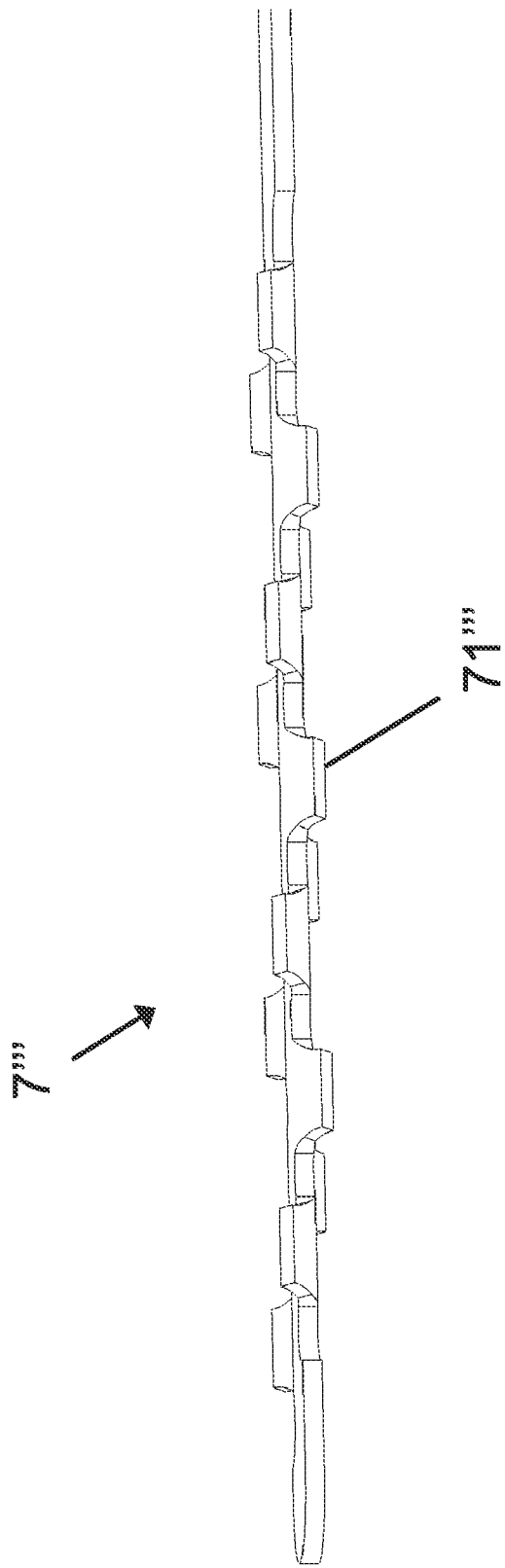

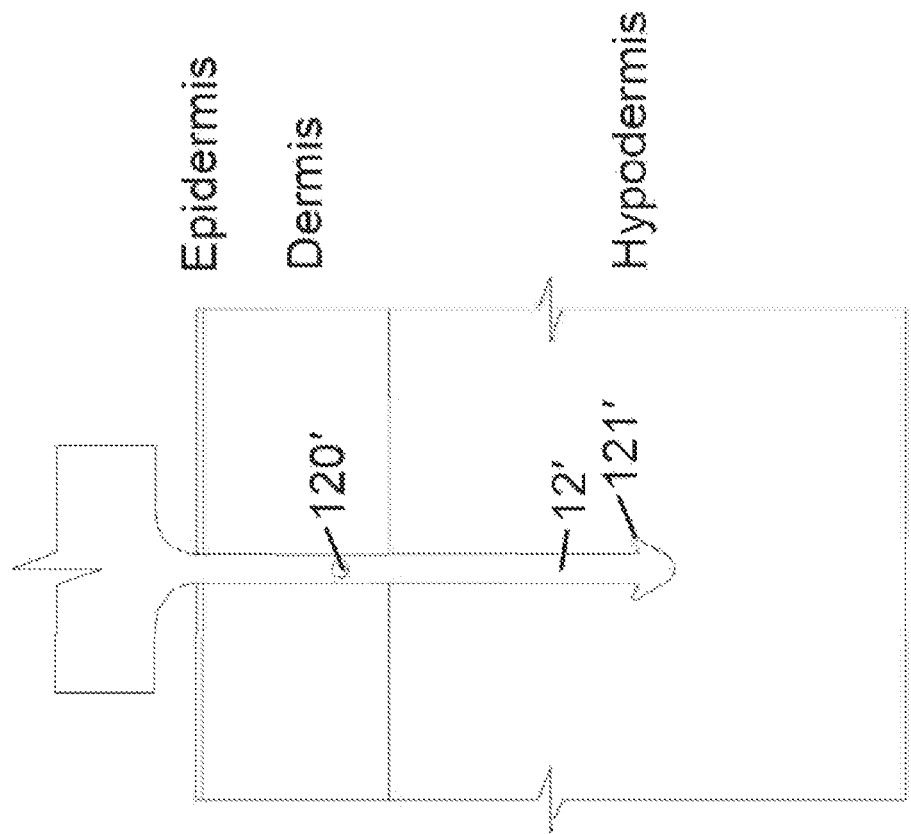
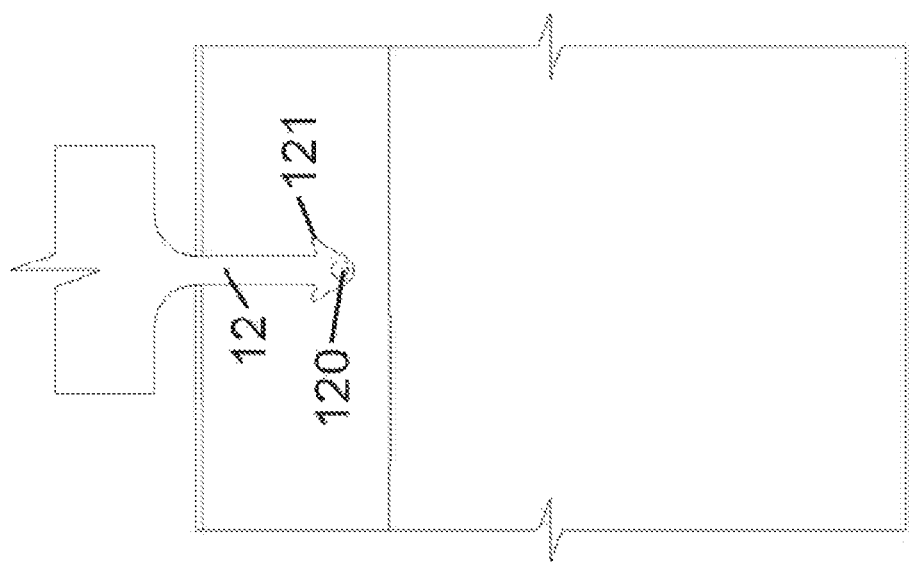
FIG. 12A
FIG. 12B

DERMAL SENSOR FOR DETERMINING ANALYTE CONCENTRATIONS

BACKGROUND

Field

The present disclosure relates to medical tools for measuring analytes, such as glucose, in the body of a subject.

Description of Related Art

Monitoring different analytes in the human body can be used for various diagnostic reasons. In particular, monitoring glucose levels is important for individuals suffering from type 1 or type 2 diabetes. People with type 1 diabetes are unable to produce insulin or produce very little insulin, while people with type 2 diabetes are resistant to the effects of insulin. Insulin is a hormone produced by the pancreas that helps regulate the flow of blood glucose from the bloodstream into the cells in the body where it can be used as a fuel. Without insulin, blood glucose can build up in the blood and lead to various symptoms and complications, including fatigue, frequent infections, cardiovascular disease, nerve damage, kidney damage, eye damage, and other issues. Individuals with type 1 or type 2 diabetes need to monitor their glucose levels in order to avoid these symptoms and complications.

Analyte monitors, and in particular, glucose monitors for the monitoring of glucose levels for the management of diabetes are constantly being developed and improved. Although there are several platforms for monitoring analytes such as glucose available on the market, there is still a need to improve their precision, wearability, and accessibility to end-users. Biosensing technologies are being increasingly explored that use different bodily fluids such as sweat and tear fluid, etc., that can be calibrated to and therefore used to measure analyte concentrations, such as blood glucose levels, accurately.

Human skin includes three layers: the epidermis, the dermis, and the hypodermis, also called the subcutaneous layer. Most or all commercially available glucose sensors on the market today sense glucose in interstitial fluid (ISF) within the subcutaneous layer, approximately 6-7 mm below the surface of the skin.

SUMMARY

There are benefits to measuring analytes such as glucose in ISF within the dermis instead of within the subcutaneous layer (hypodermis), namely a shorter equilibrium time for molecules such as glucose in the blood into the ISF in the dermis as compared to ISF within the subcutaneous layer. However, the bottom layer of the dermis is very shallow at approximately 2.5 mm below the surface of the skin, and sensors that are placed in the dermis are fairly easily pushed or pulled out of the skin. The present disclosure describes sensors with the active sensing region in the dermis, but with structural elements that provide a means to anchor the sensor structure securely within the dermis. The structural means can include structural elements within the dermis, and can also include structural elements that extend further into the body below the dermis.

An aspect of one or more embodiments of the present disclosure is directed toward a method of using a sensor to determine analyte concentrations in vivo in a subject. The method includes inserting a sensor member of the sensor into the dermis of the subject, detecting a signal associated with the analyte, and determining the concentration of the analyte from the signal. The sensor member includes a sensing region that is configured to be positioned within the dermis. The analyte detected in some embodiments can be glucose.

In an embodiment, the method further includes anchoring the sensor member in the dermis, where no part of the sensor member is configured to extend into the hypodermis of the subject.

In an embodiment, the method further includes anchoring the sensor member with anchoring means that extend into the hypodermis of the subject while the sensing region remains in the dermis.

In an embodiment, the sensor member includes barbs and/or notches configured for anchoring the sensing region in the dermis.

In an embodiment, the sensor member includes a structure that extends laterally from the bottom of the sensor member to help anchor the sensor member in the dermis.

In an embodiment, the sensor member includes plural structures that extend laterally from the sensor member to help anchor the sensor member in the dermis.

In an embodiment, the sensor member includes barbs and/or notches configured for providing anchoring for the sensor member that may extend into or may be located in the hypodermis.

In an embodiment, the sensor member includes a structure that extends laterally from the bottom of the sensor member for providing anchoring in the hypodermis while the sensing region remains positioned in the dermis.

In an embodiment, the sensor member includes plural structures that extend laterally from the sensor member to provide anchoring for the sensor member in the hypodermis, where the plural structures are configured to be positioned in the hypodermis.

In an embodiment, the sensor member includes at least some anchoring structures that extend into the hypodermis.

In an embodiment, the sensing region is inserted into the subject to a depth of about 1 mm to about 2 mm.

An aspect of one or more embodiments of the present disclosure is directed toward a sensor for determining analyte concentrations in vivo in the dermis of a subject. The sensor includes a sensor member that is insertable into the skin of the subject and that has a sensing region that is configured to be positioned within the dermis. The analyte detected in some embodiments can be glucose.

In an embodiment, the sensor member further includes a means to anchor the sensor member in the dermis, wherein no part of the sensor member is configured to extend into the hypodermis of the subject.

In an embodiment, the sensor member further includes a means to anchor the sensor member in the hypodermis of the subject.

In an embodiment, the sensor member includes barbs and/or notches configured for anchoring the sensor member in the dermis.

In an embodiment, the sensor member includes a structure that extends laterally from the bottom of the sensor member to help anchor the sensor member in the dermis.

In an embodiment, the sensor member includes plural structures that extend laterally from the sensor member to help anchor the sensor member in the dermis.

In an embodiment, the sensor member includes barbs and/or notches configured for providing anchoring for the sensor member that may extend into or may be located in the hypodermis.

In an embodiment, the sensor member includes a structure that extends laterally from the bottom of the sensor member for providing anchoring for the sensor member in the hypodermis while the sensing region itself remains positioned in the dermis.

In an embodiment, the sensor member includes plural structures that extend laterally from the sensor member to provide anchoring for the sensor member in the hypodermis, and where the plural structures are configured to be positioned in the hypodermis.

In an embodiment, the sensor member includes at least some anchoring structures that extend into the hypodermis.

According to some embodiments of the invention, a monitor for determining analyte concentrations in vivo includes a housing configured to adhere to the skin of a subject, an elongate sensor body configured to extend from the housing into the skin of the subject, an analyte sensing region positioned on the sensor body such that the analyte sensing region is configured to be held in the dermis of the skin of the subject, and at least one engagement surface configured to facilitate increased anchoring of the sensor body in the skin of the subject.

The monitor may be a glucose monitor configured to determine glucose concentrations in vivo.

The engagement surface may extend at least partially radially away from other portions of the sensor body. The engagement surface may form at least one barb element on an outer surface of the sensor body. The engagement surface may define at least one cutout in an outer surface of the sensor body. The engagement surface may form at least one arm that extends at least partially radially away from the other portions of the sensor body. The engagement surface may form a wedge that increases in width as the engagement surface extends towards a distal end of the sensor body. The engagement surface may facilitate a unidirectional insertion of the sensor body into the skin of the subject, while restricting removal of the sensor body from the skin of the subject after insertion.

The sensor body may be of a sufficient length to extend into the hypodermis of the subject without the analyte sensing region extending into the hypodermis.

The sensor body may be configured to be arranged at an acute angle relative to a bottom surface of the housing so as to extend into the skin of the subject at substantially the same angle The sensor body may extend substantially in a first plane, and wherein the engagement surface extends laterally away from the first plane.

According to some embodiments of the invention, a method of determining analyte concentrations in vivo in a subject using a monitor including a housing configured to adhere to the skin of the subject, an elongate sensor body configured to extend from the housing into the skin of the subject, an analyte sensing region positioned on the sensor body, and at least one engagement surface for anchoring the sensor body in the skin of the subject, includes adhering the housing to the skin of the subject such that the elongate sensor body extends from the housing into the skin of the subject, the analyte sensing region is held in the dermis of the skin of the subject, and the engagement surface engages the surrounding tissue to increase the anchoring of the sensor body in the skin of the subject, detecting a signal associated with the analyte in the subject, and determining a concentration of the analyte in the subject from the signal.

The monitor may include a glucose monitor configured to determine a concentration of glucose in the subject.

The sensor body may be configured to extend into the skin of the subject at an acute angle relative to the surface of the skin of the subject.

The method may further include inserting the sensor body into the skin of the subject by piercing the skin of the subject with a separate introducer and inserting the sensor body at the piercing site. The sensor body may be configured to be housed at least partially in the introducer, and wherein the introducer is removable from the piercing site while the sensor body remains inserted in the skin of the subject at the piercing site.

The sensor body may extend substantially in a first plane, and wherein the engagement surface extends laterally away from the first plane.

The engagement surface may extend at least partially radially away from other portions of the sensor body. The engagement surface may facilitate a unidirectional insertion of the sensor body into the skin of the subject, while restricting removal of the sensor body from the skin of the subject after insertion.

The sensor body may be of a sufficient length to extend into the hypodermis of the subject without the analyte sensing region extending into the hypodermis.

BRIEF DESCRIPTION OF THE DRAWINGS

Further features and advantages of the invention will become apparent from the description of embodiments by means of the accompanying drawings. In the drawings:

FIG. 11 shows a side view of the end of the analyte sensor in FIGS. 7B and 8 with teeth oriented in an alternative third configuration.

FIGS. 12A and 12B schematically illustrate analyte sensors with various lengths according to a fourth embodiment of the invention.

DETAILED DESCRIPTION

In the following detailed description, only certain embodiments of the subject matter of the present disclosure are described, by way of illustration. As those skilled in the art would recognize, the subject matter of the present disclosure may be embodied in many different forms and should not be construed as being limited to the embodiments set forth herein.

Figure 18B:
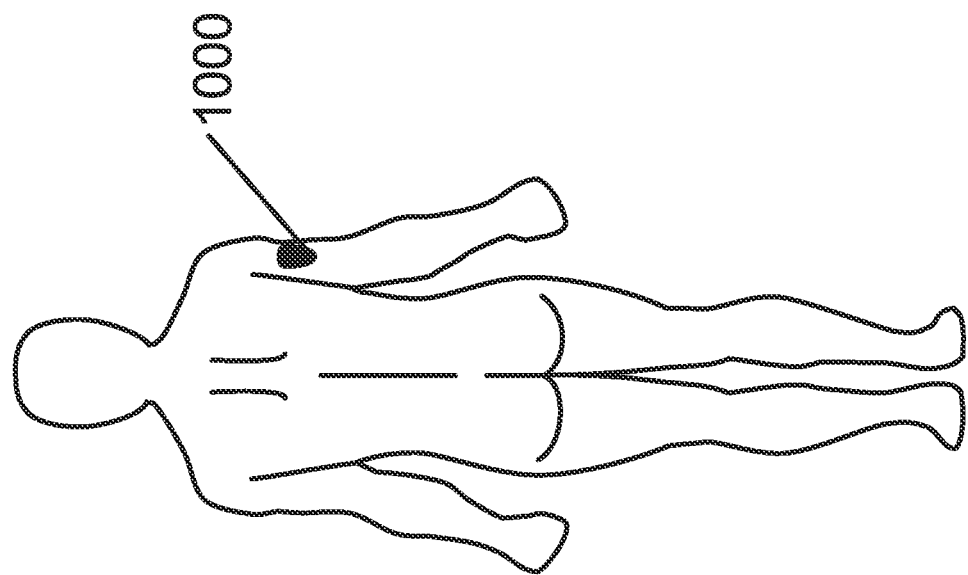
FIGS. 18A and 18B schematically show a human body with a monitor including an analyte sensor according to embodiments of the invention, where the monitor is attached at different positions on the body.
Figure 18A:
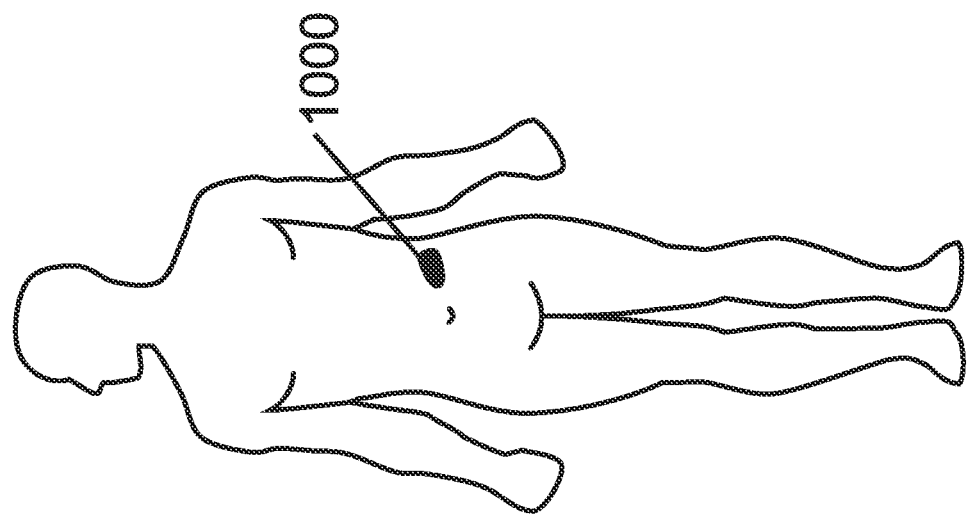

Monitors that include analyte sensors, such as glucose monitors, and particularly continuous glucose monitors, can be attached to a patient's body in different locations, in order to for example, improve glucose monitoring and/or a patient's comfort, since the continuous glucose monitors must remain adhered to the patient's skin, sometimes for a few days or more. FIG. 18A shows a first exemplary analyte monitor 1000 that is adhered to a patient's abdominal region, while FIG. 18B instead shows the exemplary analyte monitor 1000 adhered to a patient's arm. These are only meant to be example adhesion sites, and in other situations, this or a similar analyte monitor may instead be adhered or otherwise attached to other parts of the patient's body.

Figure 19:
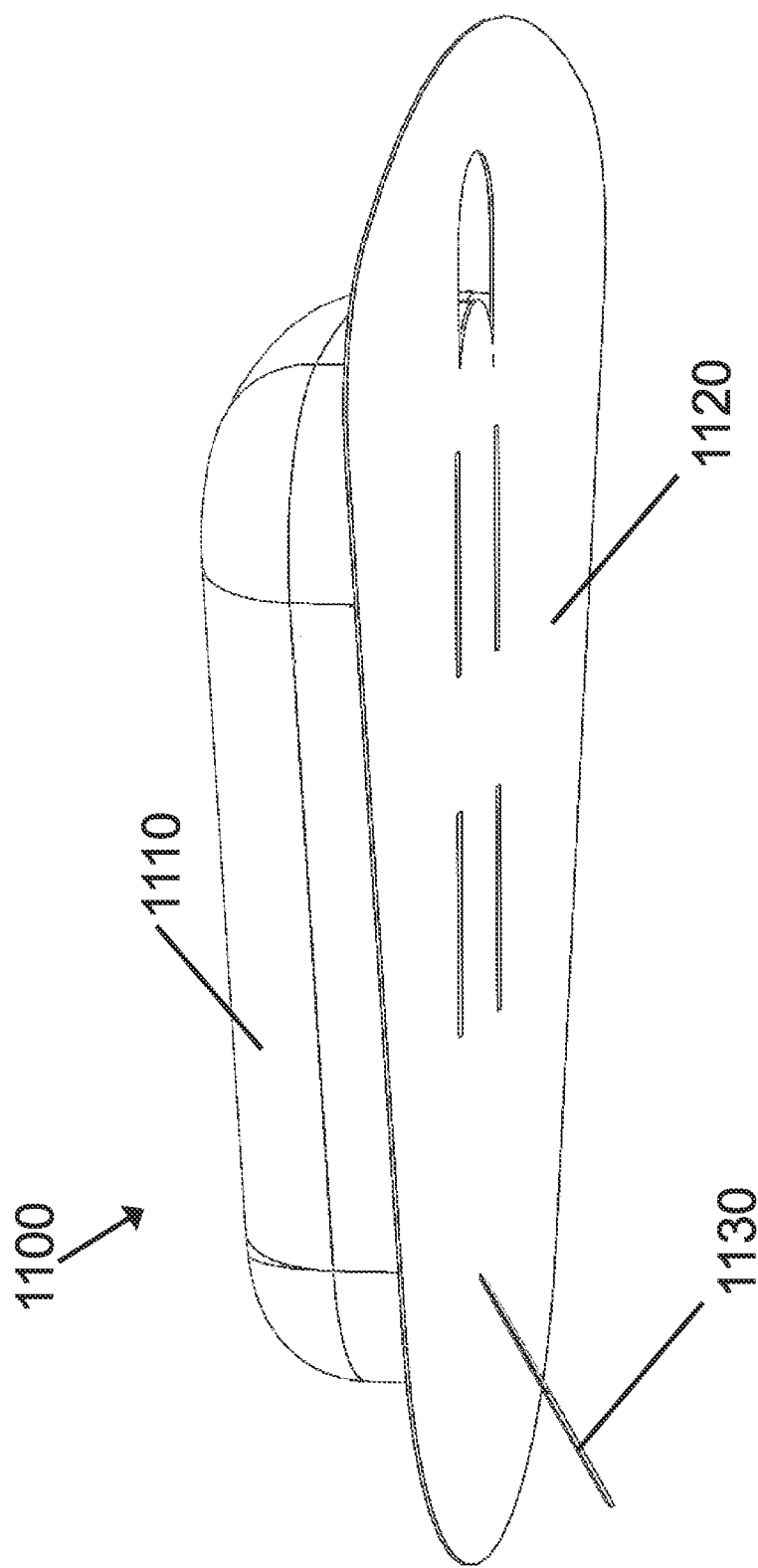
FIG. 19 shows a perspective view from below an exemplary monitor including an analyte sensor according to embodiments of the invention.
Figure 20:
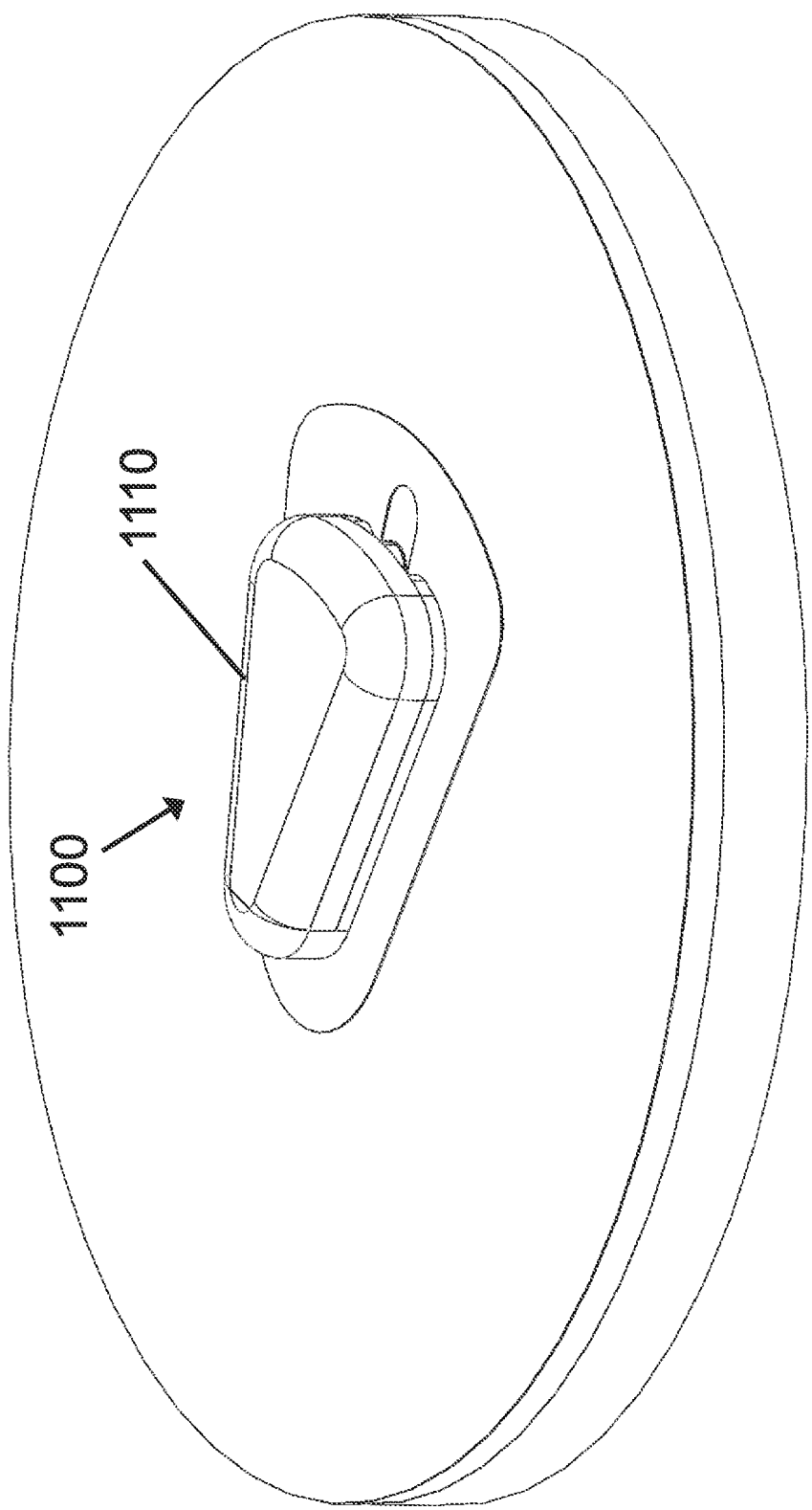
FIG. 20 shows a perspective view from above the monitor of FIG. 19, where the monitor is attached to a surface such as the skin of a patient.
Figure 21:
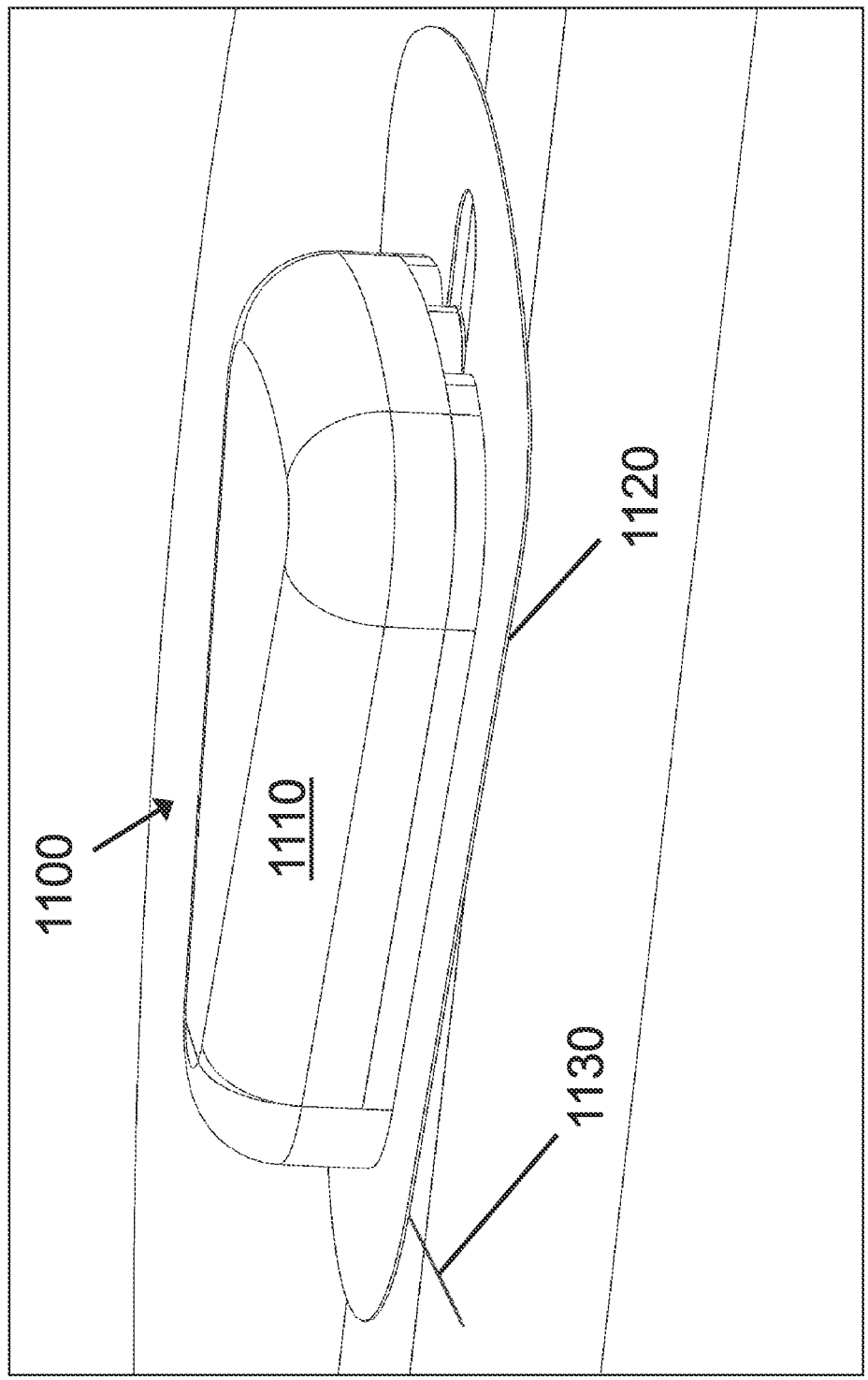
FIG. 21 shows yet another perspective view of the monitor of FIGS. 18 and 19 attached to, for example, the skin of a patient, where the analyte sensor of the monitor is schematically shown to extend into a hypodermis of the patient.

FIGS. 19 to 21 show different schematic views of an exemplary analyte monitor 1100, which can be a continuous glucose monitor, according to an embodiment of the invention. The continuous glucose monitor 1100 includes a housing 1110, an adhesive layer 1120, and a sensor member 1130 which may include an integrated needle and/or an integrated glucose sensing region.

The housing 1110 may house various components of a continuous glucose monitor or more generally an analyte monitor, for example, a circuit board or other processing means, a controller, a transmitter/receiver, and/or a battery. Different embodiments of continuous glucose monitors or other analyte monitors may include more or less components, depending on the needs of the particular monitor. Such internal components are not critical to the embodiments of the instant invention, and so further discussion of such internal components has been omitted.

An adhesive layer 1120 may be included on one side of the housing. The adhesive layer 71 may be used to adhere or otherwise attach the monitor to the patient's skin, and keep the monitor attached thereto for a prolonged period of time, for example, a few days or more. Other methods of attachment to a patient's skin may also be contemplated within the spirit and scope of the invention.

A sensor member 1130 may further be configured to protrude from a side of the housing 1110 that abuts against the patient's skin, and to pierce or otherwise extend into the patient's skin. In some embodiments, an analyte sensing region such as a glucose sensing region may be integrated directly into a needle that pierces the patient's skin, while in other embodiments, a separate piercing member may first be used to pierce the patient's skin to facilitate insertion of a sensing member 1130 including the analyte sensing region, and the piercing member may thereafter be removed, while the sensing member 1130 with the analyte sensing region remains. Various other embodiments and methods may further be used in order to provide means for the sensing member 1130 to be inserted into the patient's skin.

Figure 22:
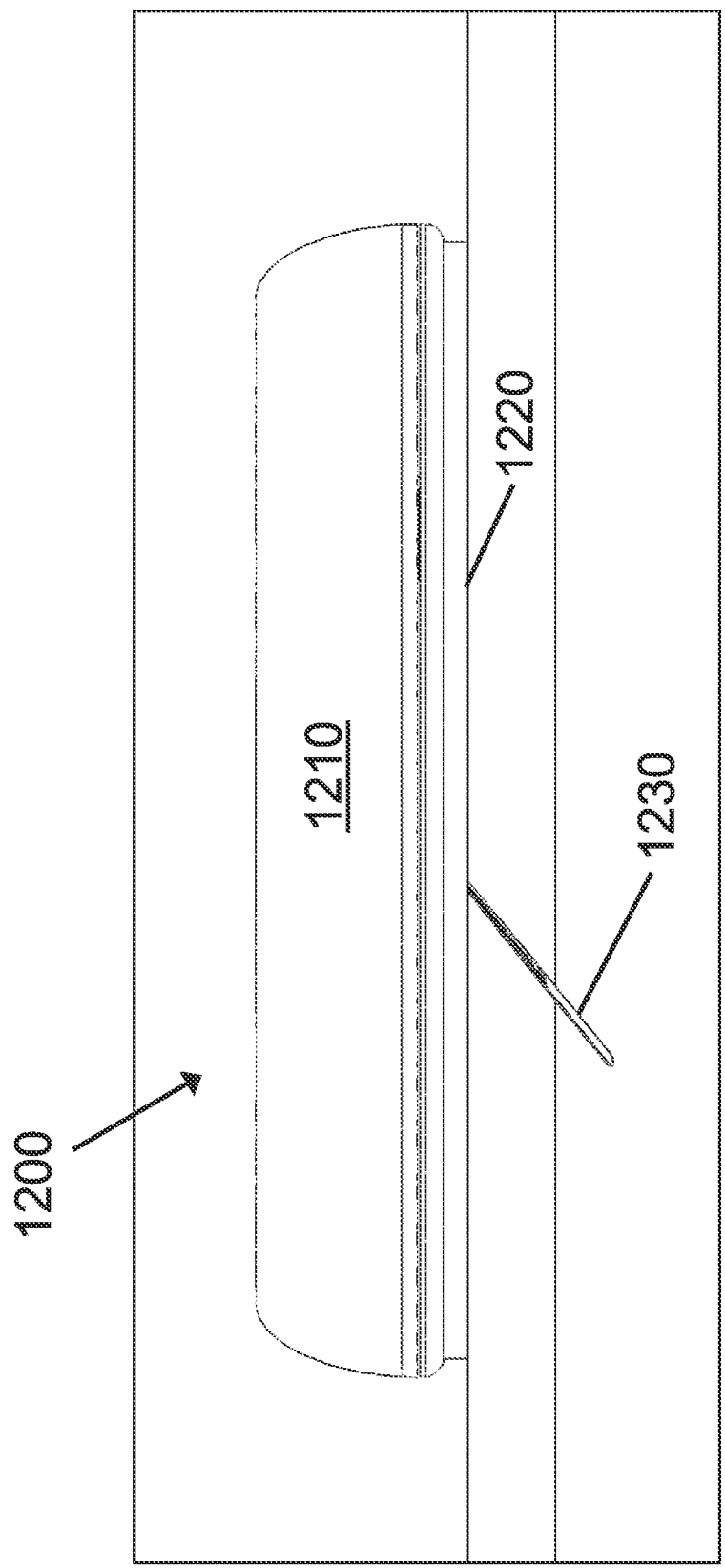
FIG. 22 shows a side view of another exemplary monitor including an analyte sensor according to embodiments of the invention that is attached to, for example, the skin of a patient, where the analyte sensor is schematically shown to extend into a hypodermis of the patient.

By way of example, FIG. 22 shows a side view of another exemplary monitor including an analyte sensor according to embodiments of the invention, where the monitor is attached to, for example, the skin of a patient, and where the analyte sensor is schematically shown to extend into a hypodermis of the patient. The analyte monitor 1200 includes a differently shaped housing 1210, which may be, for example, circular or puck shaped, a similar adhesive layer 1220 for adhering the monitor to a patient's skin, and a sensor member 1230 which extends into the patient's skin when the monitor is deployed. Here, the sensor member 1230 extends from a more centrally located region of the housing 1210 instead of closer to one end of the housing. Any other housing, sensor member or sensing region location, and/or any of various other properties and characteristics of different analyte monitors may also be contemplated without departing from the spirit and scope of the invention. For example, in some embodiments, the sensor member may be deployed at a more right angle relative to the skin of the patient, or at a different angle than the angle shown. Other variations are also contemplated to be used together with the invention.

Figures 1A, 1B:
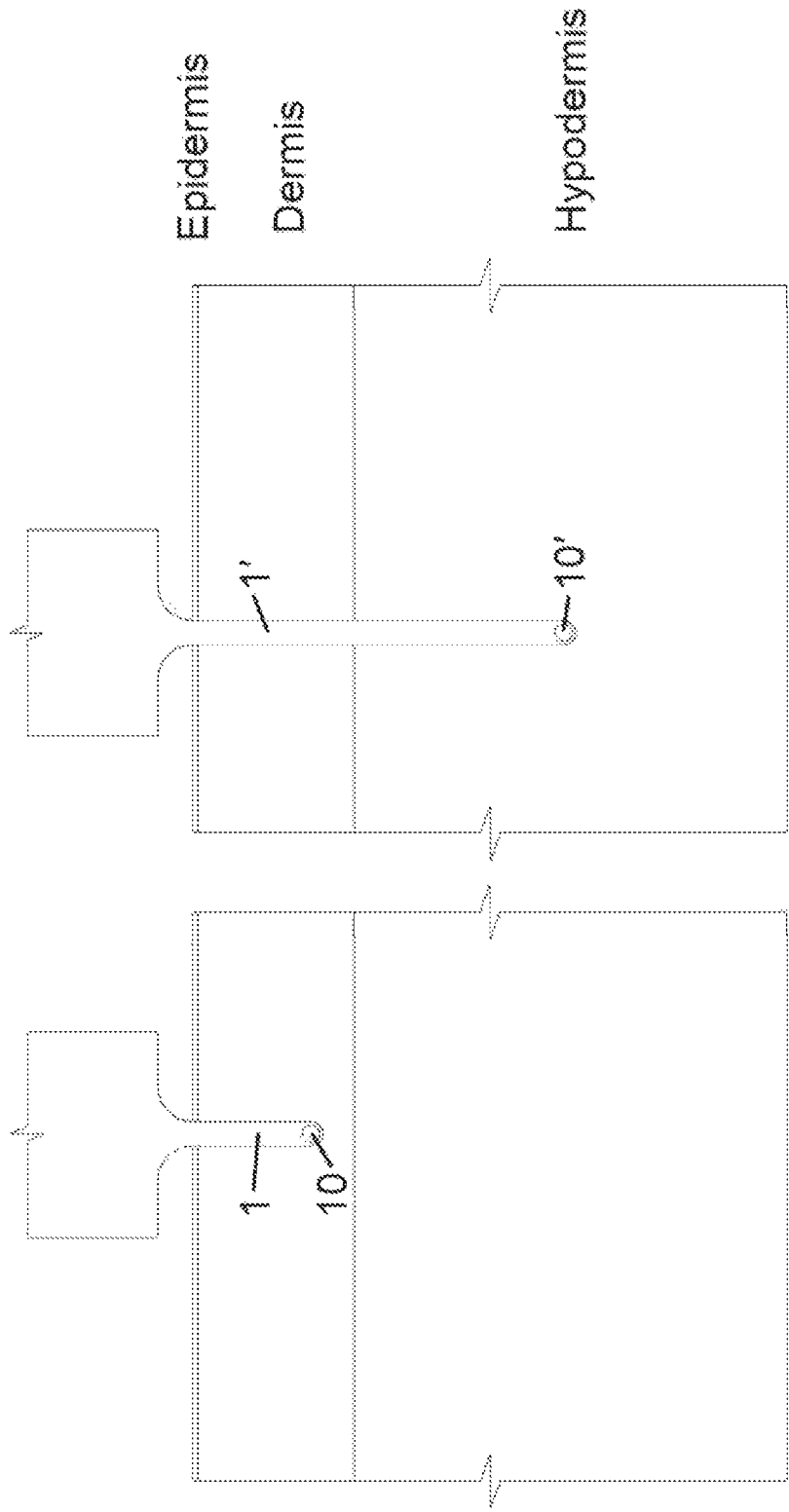
FIGS. 1A and 1B provide schematic illustrations of analyte sensor arrangements.

Referring now back to FIGS. 1A and 1B, both FIGS. 1A and 1B illustrate more traditional sensor member arrangements. As previously noted, most or all commercially available glucose sensors on the market today sense glucose in the ISF within the hypodermis or subcutaneous layer, approximately 6-7 mm below the surface of the skin. FIG. 1B shows a typical arrangement of such a sensor member 1', where the sensor member is elongate and where placement of a glucose sensing region 10' is near a free end or tip of the sensor member 1', such that the glucose sensing region 10' is positioned in the hypodermis, well away from the dermis of the skin.

However, contrary to the more traditional analyte sensors that measure analytes such as glucose in the hypodermis, there are benefits to measuring glucose and/or other analytes in the interstitial fluid in the dermis instead. For example, there is a shorter equilibrium time for glucose in the blood into the interstitial fluid in the dermis as compared to the hypodermis. FIG. 1A illustrates another example of a sensor member 1, where sensing in the dermis is possible. Similar to FIG. 1B, a glucose sensing region or other analyte sensing region 10 is placed near a free end or tip of the sensor member 1, based on a common sensing region placement or arrangement in existing sensors.

However, the bottom boundary of the dermis is very shallow from the surface of the skin, for example, approximately 2.5 mm below the surface of the skin. Therefore, in traditional devices like those illustrated in FIG. 1A, where the analyte sensing region 10 is located at or near a tip of the sensor member 1 and where the sensor member 1 including the analyte sensing region 10 are all intended to be housed in the dermis, the total length of the sensor member must be made very short, for example, less than 2.5 mm in total length. Such an arrangement raises the issue of unintended pushing or pulling, or otherwise unintended withdrawal, of the sensor member from the patient's skin due, for example, to general movement by the patient or other factors.

Embodiments of the invention therefore provide a sensor arrangement which will allow an analyte sensing region such as a glucose sensing region to be positioned in the dermis of a patient's skin, while facilitating more secure holding of the sensor member, thereby allowing the sensor to remain more securely in place for hours, days, or longer, while the subject conducts his or her daily activities or routines.

Figure 2:
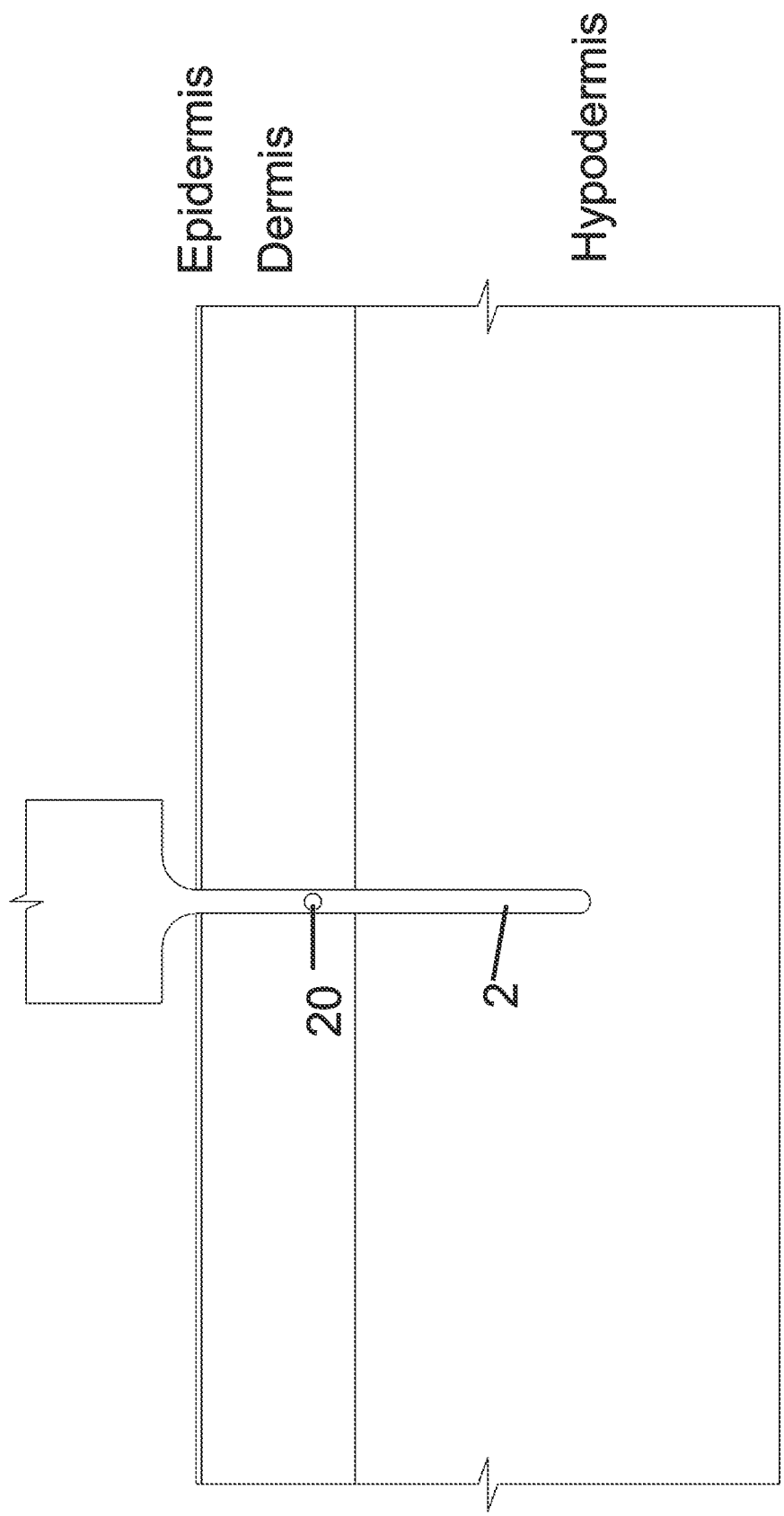
FIG. 2 schematically illustrates an analyte sensor according to a first embodiment of the invention.

FIG. 2 schematically illustrates a sensor member or sensor body 2 according to a first embodiment of the invention. The sensor member 2 in FIG. 2 is similar to the sensor member 1' illustrated in FIG. 1B, where the free end of the sensor member extends into the hypodermis of the patient's skin. However, the sensor member 2 differs from the sensor member 1' in the placement or positioning of the analyte sensing region (e.g., a glucose sensing region), where analyte sensing region 20 is placed more proximally on the sensor member 2, at a depth that corresponds to the dermis of the patient's skin when the sensor member 2 is fully implanted into a patient's skin, for example, when the analyte monitor is fully adhered to the skin. Such a depth may be, for example, 1 mm to 2 mm under a surface of the patient's skin. Since the sensor member 2 extends into the hypodermis, the sensor member 2 can be more securely placed and held under the patient's skin, as compared to, for example, the shorter sensor member 1 in FIG. 1A, while the alternative placement of the analyte sensing region 20 provides the benefits of analyte sensing in the dermal region. In this embodiment, dislodging of the sensor member 2 from the patient's skin is more difficult due to the length of implantation of the sensor member 2, where a much larger force or pullout distance is required to pull or push the sensor member out of the body. Other variations to such an arrangement have also been contemplated. For example, in some embodiments, the sensor member 2 may be made of a more rigid material, such as for example, a biocompatible stainless steel, and can be used to pierce and directly implant into a patient's skin. Meanwhile, in other embodiments, the sensor member 2 can be made of a more flexible material, for example, a biocompatible polyimide, to improve comfort of the patient since the implantation depth is deeper. In the latter embodiments, for example, a separate piercing member may be used to pierce the skin, and thereafter withdrawn while the sensor member 2 remains under the patient's skin. Some embodiments may be arranged, for example, with a hollow needle that acts as a piercing member, and with the sensor member 2 housed within the hollow needle, where the two components are implanted together into the patient's skin, and where the hollow needle is removed after the sensor member 2 is located at a desired position or depth. As shown, the sensor member 2 is implanted into the patient's skin substantially perpendicularly to the patient's skin in FIG. 2. However, with this as with the embodiments of the invention that follow, the sensor member 2 may also be inserted into the patient's skin at an angle that deviates from being perpendicular to the patient's skin, as will be described in greater detail below.

Figure 3A:
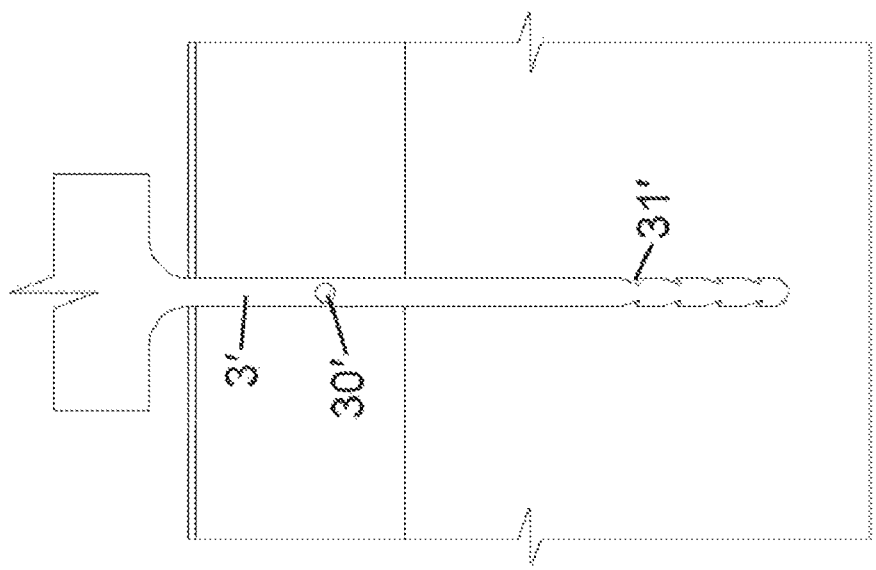
FIGS. 3A and 3B schematically illustrate analyte sensors with various lengths according to a second embodiment of the invention.
Figure 3B:
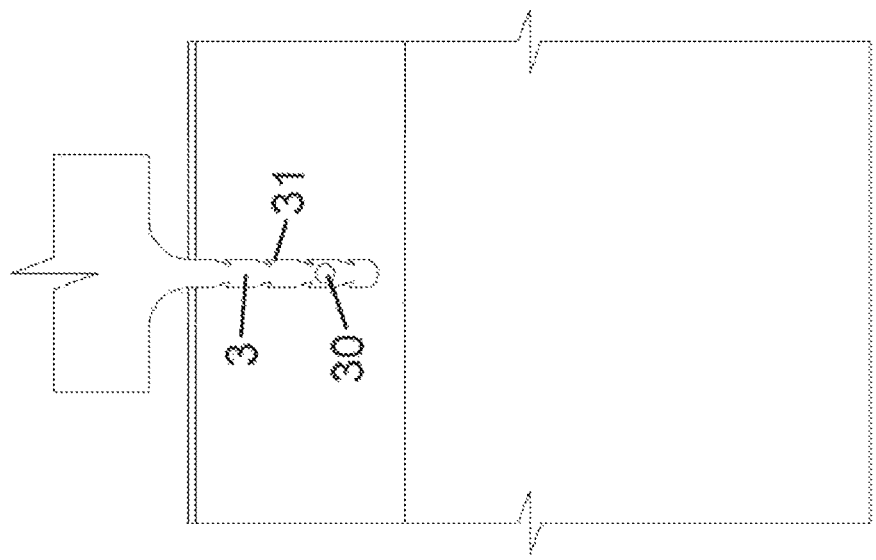

FIGS. 3A and 3B illustrate sensor members according to a second embodiment of the invention. FIG. 3A provides an option for a shorter sensor member 3 with a length that only extends into the dermis of a patient. However, unlike sensor member 1 in FIG. 1A, sensor member 3 includes, on its outer surface, a surface feature or features 31 that help more securely anchor the sensor member in the skin at a desired depth. The surface features may include backward facing notches, barbs, or hooks, for example, that result in sharp edges that catch and/or otherwise engage in the flesh when the sensor member is pushed or pulled relative to the patient's body. Such backward facing notches or barbs, or any other unidirectional feature, may facilitate insertion of the sensor member 3 in a distal direction into the skin, but then dig in or otherwise engage the patient's flesh to restrict pulling out of the sensor member 3 once implanted in the skin. The barbs or notches may be formed at the same circumferential position around an axis of the sensor member, or may be formed at different circumferential positions and/or different axial positions on the sensor member. Other embodiments may include any other arrangement where it may be easier to insert the sensor member 3 than it is to retract the sensor member 3 out of the skin. In some other embodiments, it is also contemplated that the surface features 31 may not be unidirectional. For example, the surface features 31 may hinder movement of the sensor member 3 in both insertion and removal directions. Such embodiments may be more suitable, for example, for use together with a separate piercing member which covers the surface features 31 during insertion, so as not to hinder implantation of the sensor member 3.

In some embodiments, the barb arrangement may, for example, resemble a stinger on honey bees, with backward facing barbs that facilitate puncturing of the sensor member into the skin, but that prevent or otherwise hinder pulling out of the sensor member after implantation. By way of analogy, on a bee stinger, the backward facing barbs result in a force required to extract the stinger being approximately 20 times greater than the force required to insert the stinger. A similar arrangement on a sensor member will help facilitate a more stable and constant implantation and holding of the sensor member in a patient's skin after implantation.

In such manner, a surface feature that forms an anchoring means can be incorporated into the sensor member 3, in order to increase or otherwise enhance the hold of the sensor member 3 in the patient's skin. The arrangement in FIG. 3B provides a similar arrangement to FIG. 3A, except that the sensor member 3' is longer and is configured to extend into the hypodermis of the patient's skin. Here, similarly as seen in the embodiment of FIG. 2, the sensing region 30' may be positioned more proximally on the sensor member 3', so as to be positioned in the dermis even when the sensor member 3' is fully inserted into the patient's skin. Meanwhile, the distal tip of the sensor member 3' is configured to extend into the hypodermis. Similar barbs or notches or other surface features 31' may be formed on the outer surface near the tip or free end of the sensor member 3', such that the surface features engage the hypodermis. In other embodiments, similar barbs, notches, or other surface features may also only be formed on the sensor member at a depth corresponding to the dermis of the patient's skin, or in still other embodiments, may be formed at depths corresponding to both the dermis and the hypodermis of the patient's skin. Similarly as discussed with respect to the embodiment in FIG. 2, the embodiments of sensor members 3, 3' shown in FIGS. 3A-3B may also be made of either a more rigid or of a more flexible material. Such arrangements and material selections may be made and selected based on, for example, the desired level of engagement/attachment and/or abrasiveness or comfort level of each individual patient.

As noted above, additional anchoring means such as barbs or notches can be incorporated into the outer surfaces of the sensor members according to embodiments of the invention, in order to enhance and form a more stable engagement between the sensor member and the patient's skin, and to reduce the occurrence of backing out of the sensor member after implantation, which will help provide a more consistent continuous glucose monitor reading, for example, in the case of a glucose monitor. Such anchoring means may serve to substantially increase the force required to withdraw the sensor member from the body, even though the sensing region itself is positioned relatively shallowly in the dermis of the patient's skin. It is envisioned that by adding barbs or notches, adjusting a number of such surface features that are formed on the sensor member, and/or adjusting such surface features to remain in a same plane as the rest of the sensor body or to project out of or away from the plane in any of various different directions, that a desired level of engagement between the sensor member and the patient's skin can be achieved, without unnecessarily irritating or otherwise damaging the patient's skin. In the described embodiments, the barbs or notches may be integrally formed on or in the outer surface of the sensor member. In other embodiments, for example, separate barb elements may be attached to the body of the sensor member by deposition, adhesion, or some other type of attachment means.

Furthermore, the structural features that help anchor the sensor member are not limited to one particular type or those types previously discussed herein, and one or more different types of surface features may be used on a same sensor member to improve anchoring of the sensor member. The types of edges, barbs, etc. between different embodiments may also be different. The sensor member itself and/or the surface feature or other anchoring means may be formed with either relatively flexible material or stiffer materials, and may be made of the same or of different materials from one another.

In addition, the placement of the analyte sensing region relative to the surface anchoring features may differ as well. For example, in FIG. 3A, the sensing region 30 is positioned near a tip of the sensor member 3, distal to at least some of the surface features 31. But in other embodiments, the sensing region 30 may be formed more proximally, such that more of the surface features 31 are located distal to the sensing region, or the sensing region may be formed proximal to all of the surface features 31. As an alternative example, as can be seen in FIG. 3B, the sensing region 30' which is configured to be positioned in the dermis, is formed proximally to the surface anchoring features 31' which are configured to engage in the hypodermis. Even here, in embodiments where the surface features 31' extend into the dermis, the sensing region 30' may be formed at a same axial height as at least some of the surface features 31', or may be formed entirely distal to the surface features 31' if the surface features 31' are only formed to engage the patient's dermis.

Figure 4:
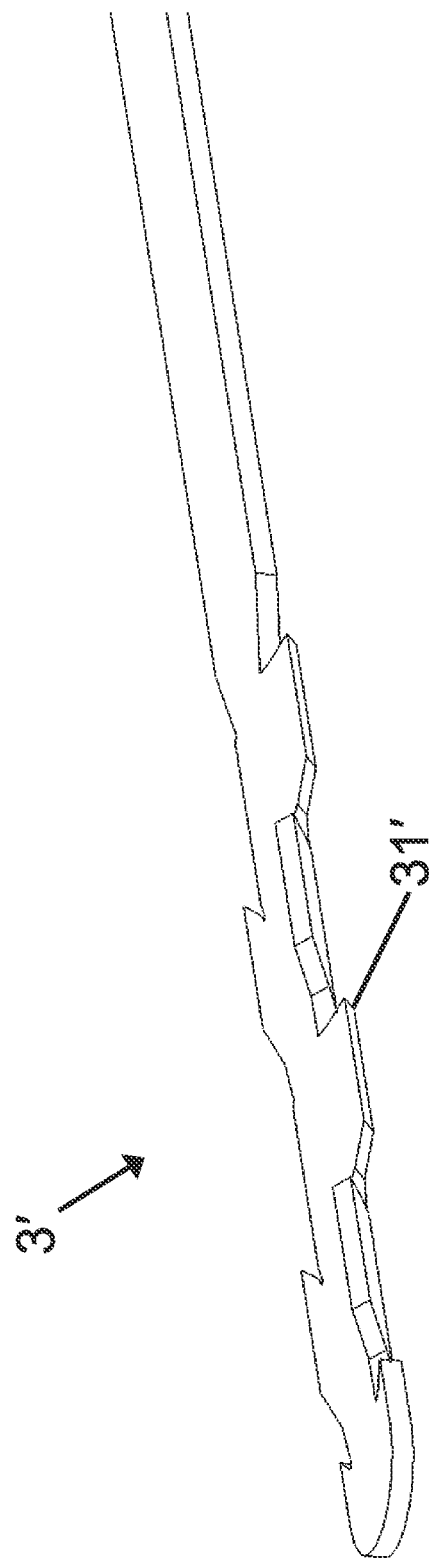
FIG. 4 shows a perspective view of an end of the analyte sensor in FIGS. 3A and/or 3B.
Figure 5:
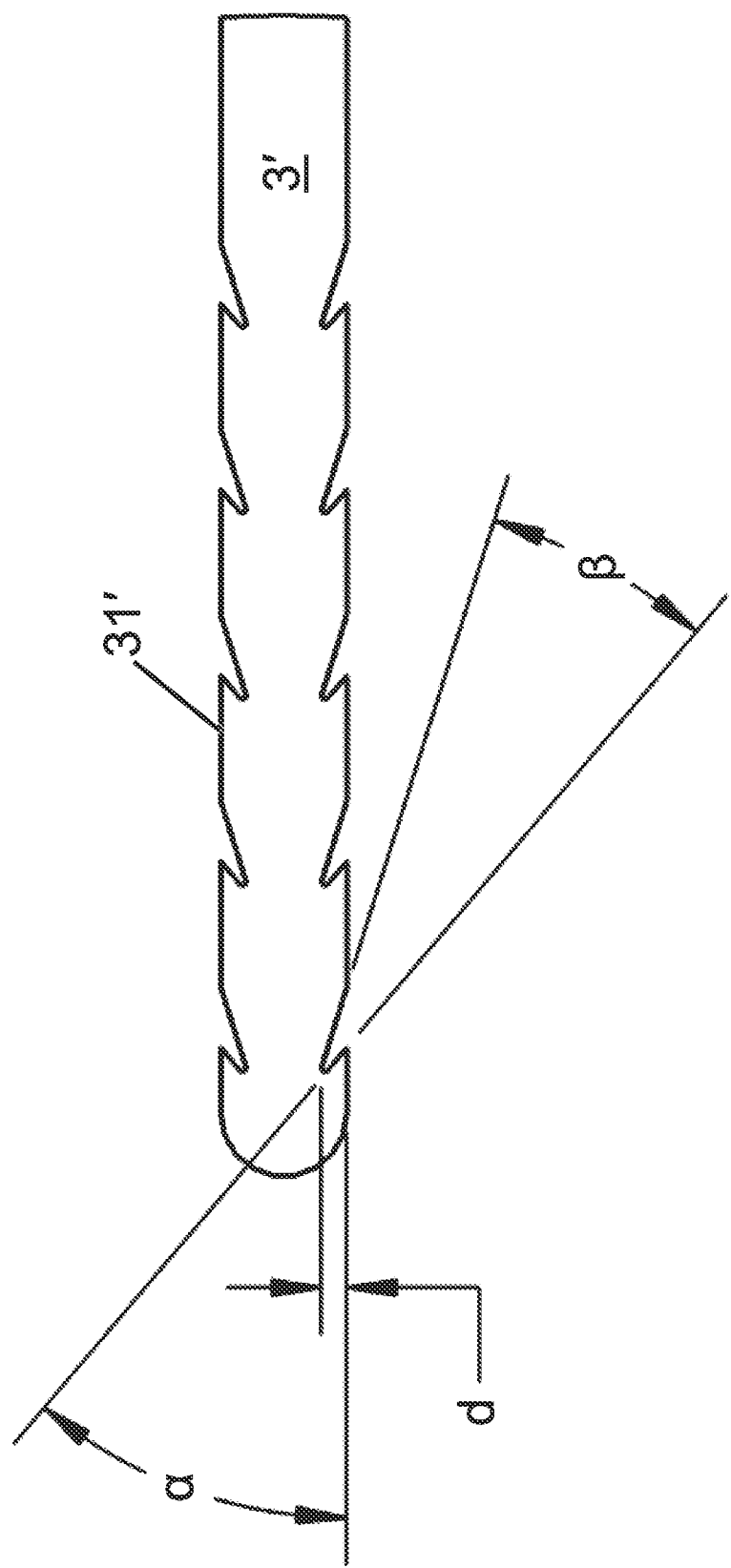
FIG. 5 shows a side view of the end of the analyte sensor in FIG. 4.
Figure 6:
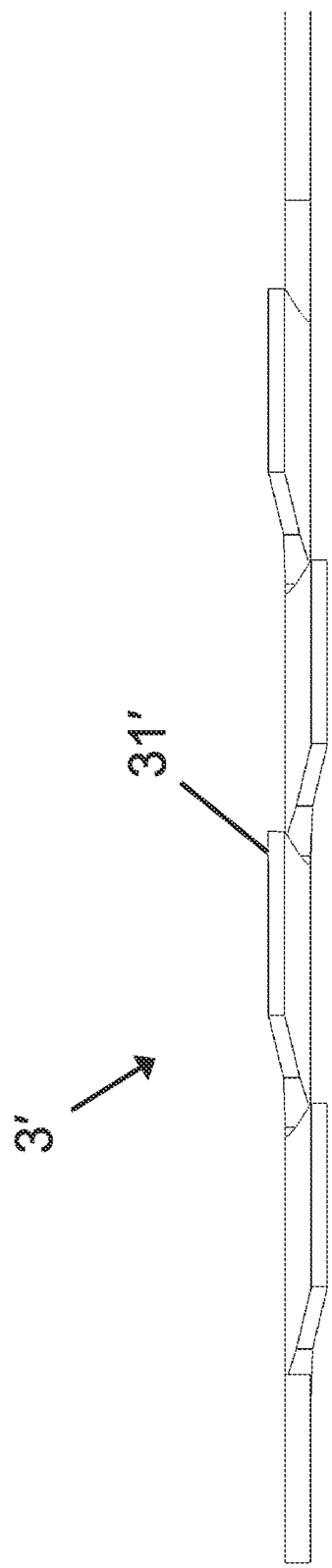
FIG. 6 shows a side view of the end of the analyte sensor in FIGS. 4 and 5, where the side view is rotated 90° relative to the side view of FIG. 5.

FIGS. 4 to 6 show additional different views of the distal end of the sensor member 3' from FIG. 3B, including at least some of the surface features 31'. As noted before, sensor member 3' includes barbs 31' that extend laterally from the sensor member. In the embodiment shown, the barbs are further angled away from a plane of the sensor member, and alternate in their directions of angulation. In other words, the sensor member 3' may extend in a plane of extension, and a first row of surface features 31' may be angled away from a first side of the plane (e.g., downwardly in FIG. 6), while a second row of surface features 31' may then be angled away from an opposite second side of the plane (e.g., upwardly in FIG. 6). The remaining rows of barbs or other surface features 31' may then extend away from the plane of the sensor member 3' in an alternating manner. In other embodiments, the surface features may not extend away from a plane of extension of the sensor member at all, while in still other embodiments, the surface features may extend away from the plane of the sensor member all in a same direction or in varying different patterns or sequences.

Furthermore, as shown in FIG. 5, barbs based on different embodiments of the invention may have, for example, different depths, and different angular constructs. In an exemplary embodiment, a width of the sensor member may be, for example, 350 µm, while a depth d of the barb may be formed to be, for example, 75 µm, or in other embodiments, within a range of about 5% to about 40% of the entire width of the sensor member. The leading edge of the barb may, in some embodiments be angled at an angle α which may be, for example, 45° to a longitudinal axis of the sensor member, but may alternatively be more or less than 45° in other embodiments. Both the leading edge and the trailing edge of the barbs may further be arranged at different angles, such that, for example, another angle ß which may be approximately 25° is formed between the two edges of the barbs, where in other embodiments the angle β formed between the two edges of the barbs may be more or less than 25°. The embodiments of the invention are not limited to these disclosed measurements, and one skilled in the art will recognize that the measurements can deviate from these examples without departing from the spirit or scope of the invention.

Figure 7:
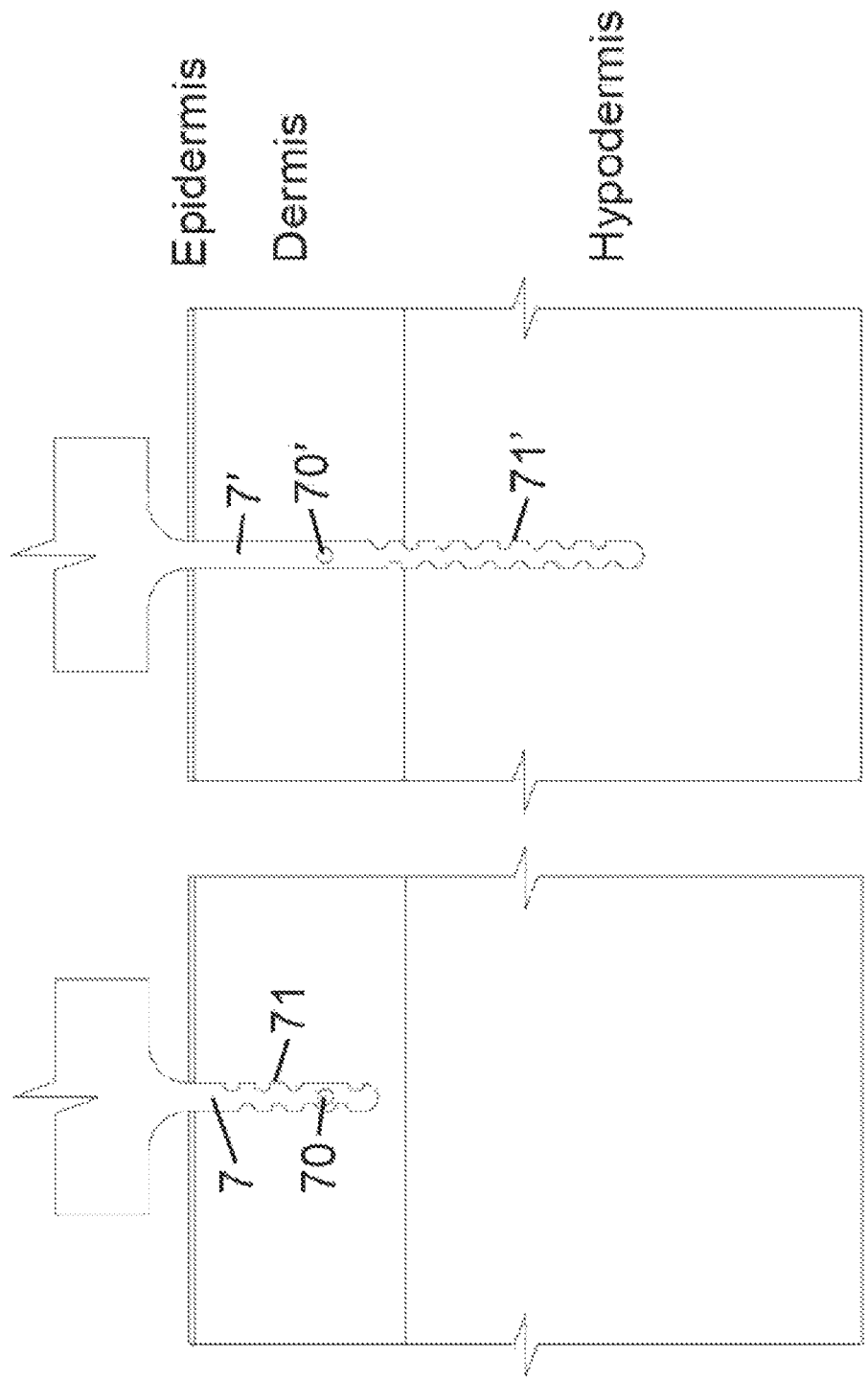
FIGS. 7A and 7B schematically illustrate analyte sensors with various lengths according to a third embodiment of the invention.
Figure 8:
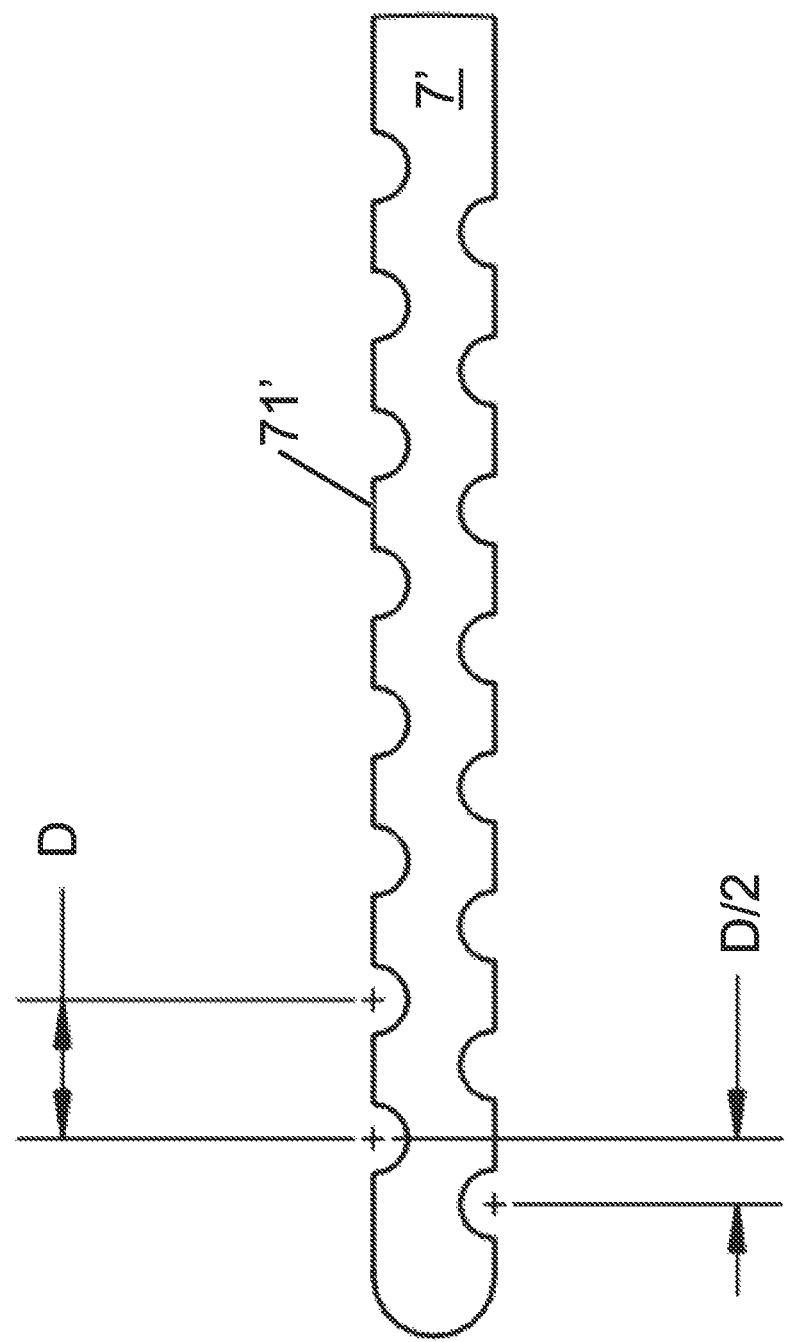
FIG. 8 shows a side view of an end of the analyte sensor in FIGS. 7A and/or 7B.

FIGS. 7A to 11 illustrate sensor members according to a third embodiment of the invention. Similar to the embodiment shown in FIGS. 3A and 3B, FIG. 7A shows an embodiment where a sensor member is shorter and configured to only extend into a dermis of a patient's skin when fully implanted, while FIG. 7B shows a longer arrangement where the sensor member is long enough to extend into the hypodermis of the patient's skin. In both embodiments shown in FIGS. 7A and 7B, instead of barbs, the sensor members 7, 7' include surface features arranged in a staggered sawtooth arrangement. For example, as more clearly seen in FIG. 8, the sawtooth arrangement may include cutouts in the form of semicircles that are formed at edges of the sensor member 7, 7'. In the embodiment shown, the cutouts or recesses are staggered along a length of the sensor member 7, 7', such that teeth 71, 71' are formed along a length of the sensor member. The teeth, like the cutouts, may be arranged in a staggered form along the sides of the sensor member, where for example, an axial distance D may separate cutouts on a same side of the sensor member, while an axial distance between adjacent cutouts on opposite sides of the sensor member may be half of that distance, or D/2. However, in other embodiments, the cutouts and resulting teeth may also, for example, be arranged in a manner where opposing cutouts are aligned with one another and opposing teeth are therefore also aligned with one another. It is noted, however, that the staggered sawtooth arrangement may be advantageous, for example, sensor members with the staggered arrangement may be stronger and less likely to tear since the cutouts would not form unnecessary narrow weak points along the length of the sensor member. Other sawtooth arrangements may further be contemplated. In still other embodiments, the cutouts may be formed by, for example, less or more or a circle, or of any other suitable shape that can form teeth which are capable of lodging in a patient's skin to improve anchoring. Furthermore, the depth of the cutouts may be limited, such that a width of the sensor member between the cutouts remains at least a certain width, for example, 20% or more, in order to maintain a sufficient structural integrity or robustness of the sensor member.

Referring back to FIGS. 7A and 7B, the sawtooth arrangement 71 in FIG. 7A is configured to be contained entirely in the dermis based on the shortened length of the sensor member 7, with the analyte sensing region 70 located close to a distal end of the sensor member 7. Similarly as discussed with respect to FIG. 3A, in other embodiments, the sensing region 70 may be located at different axial positions in other embodiments, for example, at a distalmost tip of the sensor member, or more proximally so that most or all of the teeth 71 of the sawtooth arrangement are configured to be located distally to the sensing region. Meanwhile, in FIG. 7B, while the sensing region 70' is located to sense analytes in the dermis, the sensor member 7' extends into the hypodermis, where most or all of the teeth 71' are configured to be located in the hypodermis. In some embodiments, all of the teeth 71' will engage the hypodermis, whereas in other embodiments like the one shown in FIG. 7B, one or more of the teeth 71' may extend proximally into the dermis as well. In still other embodiments, even if the sensor member extends into the hypodermis, most or all of the teeth of the sawtooth arrangement may instead be formed to engage the dermis instead of the hypodermis. The arrangement of teeth will generally depend, for example, on the level of engagement with the patient's skin sought by the manufacturer, practitioner, and/or patient.

Figure 9:
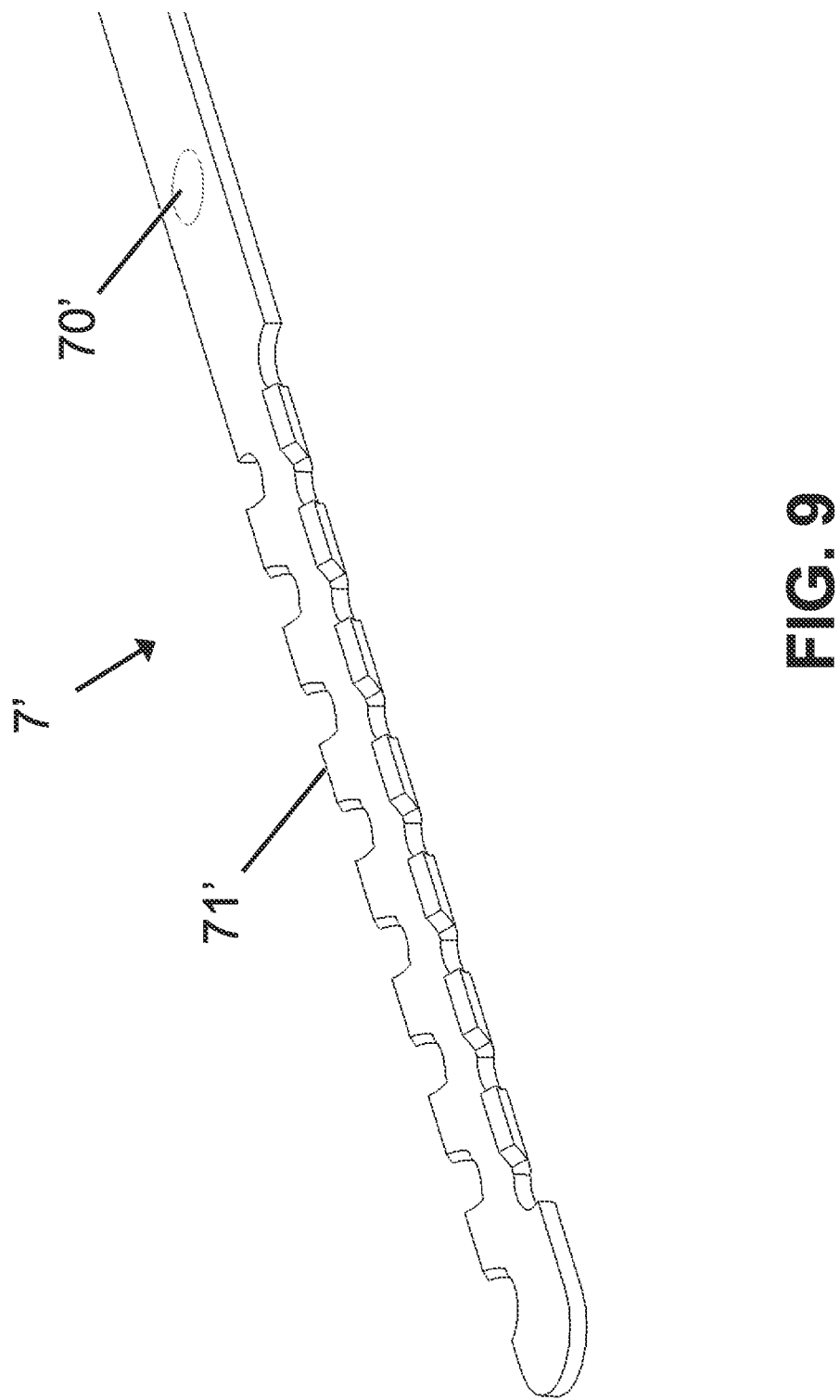
FIG. 9 shows a perspective view of the end of the analyte sensor in FIGS. 7B and 8 with teeth oriented in a first configuration.
Figure 10:
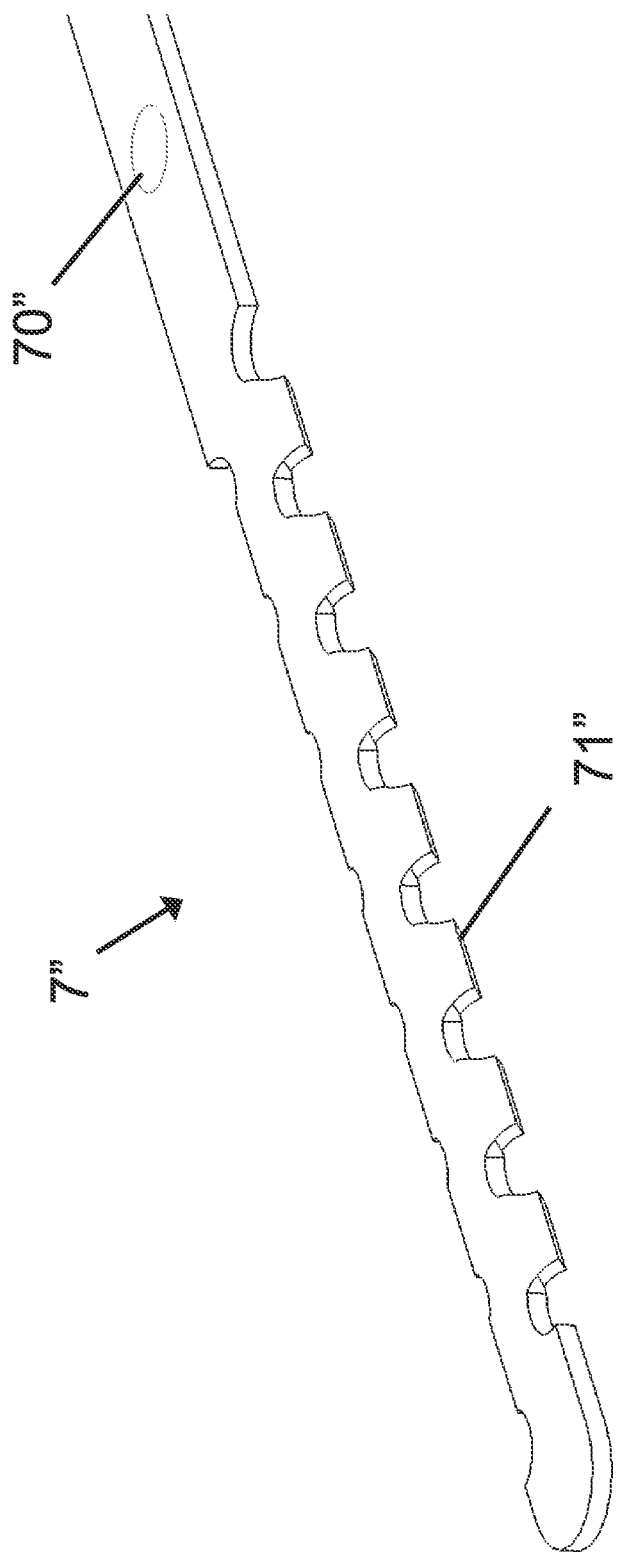
FIG. 10 shows a perspective view of the end of the analyte sensor in FIGS. 7B and 8 with teeth oriented in an alternative second configuration.

FIGS. 9, 10, and 11 respectively show three different arrangements of teeth in the sawtooth embodiment of FIG. 7B. As seen in FIGS. 9 and 10, all of the teeth extend out of the plane of the sensor member 7', 7" on a same side of the plane. Such an arrangement may be advantageous, for example, in order to further increase an anchor strength of the sensor member in a patient's skin when compared, for example, to a fully flat or planar sensor member. In FIG. 9, all of the teeth 71' extend away from the plane of the sensor body 7' on a side of the sensor body on which the sensing region 70' is formed. Conversely, in FIG. 10, all of the teeth 71" extend away from the plane of the sensor body 7" on an opposite side of the sensor body from FIG. 9, that is, on a side of the sensor body 7" opposite to the side on which the sensing region 70" is formed. FIG. 11 shows another different arrangement of the teeth 71''' of the sawtooth feature, where the teeth 71''' on a further embodiment of sensor body 7'''' are arranged in an alternating manner similar to that described above with respect to the barbs in FIGS. 4 to 6. The alternating arrangement of the sensor body 7''' in FIG. 11 may be advantageous over the arrangements in FIGS. 9 and 10, for example, due to an even greater anchoring strength. On the other hand, the arrangements in FIGS. 9 and 10 may also have advantages over the arrangement in FIG. 11, for example, easier manufacturing and/or easier insertion. Various other configurations of teeth in similar sawtooth arrangements according to embodiments of the invention may further be envisioned.

Figure 13:
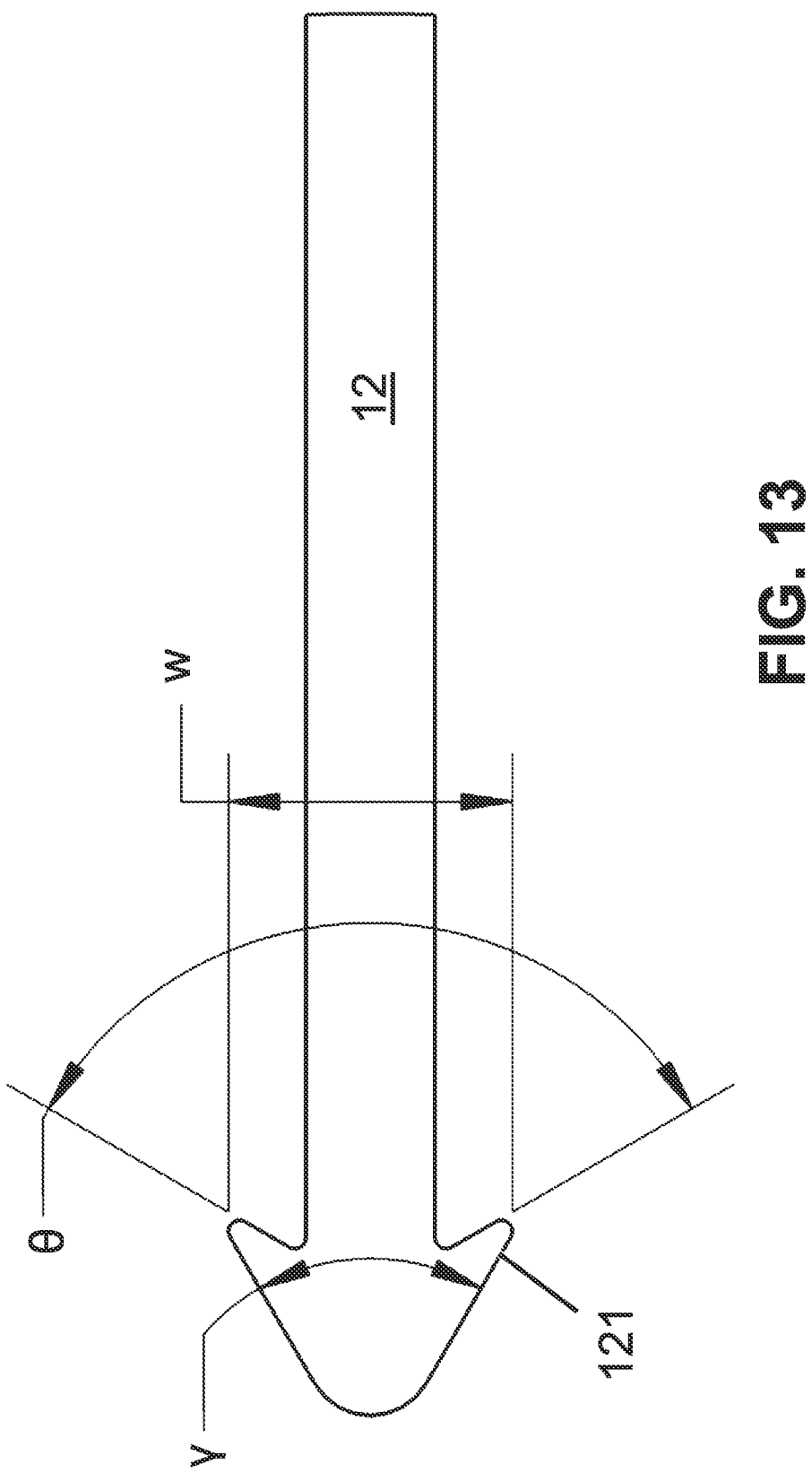
FIG. 13 shows a side view of an end of the analyte sensor in FIGS. 12A and/or 12B.

FIGS. 12A to 13 show still further sensor members according to a fourth embodiment of the invention. First, as shown in FIG. 12A, the entire sensor member 12 is again relatively short, and is configured to extend only into the dermis of a patient's skin. Here, no part of the sensor member 12 extends into the hypodermis or subcutaneous layer. The sensor member 12 has an analyte sensing region 120 that is located at or near the tip or free end of the sensor member 12, where due to the shorter length of the sensor member 12, would still position the analyte sensing region 120 in the dermis. The sensor member further includes a structural feature 121 that helps to anchor the sensor member in the patient's body. The feature in this embodiment includes a structure 121 that extends at least partially transversely away from the central region of the sensor member 12 in a radial direction. Here, the structure 121 includes two arms, for example, that extend away from opposite sides of the sensor member 12 at or near the tip or free end of the sensor member 12. In the embodiment of FIG. 12A, the arms 121 extend at an angle that points back towards the proximal end of the sensor member 12, such that the tapers formed by the arms 121 allow for easier insertion into the skin, while preventing or otherwise hindering pullback to prevent unintended removal of the sensor member 12 from the skin once implanted. However, in other embodiments, the arms may instead extend, for example, horizontally from the central region of the sensor member, or at any other suitable angle that will help reduce the possibility of inadvertent dislodging of the sensor member 12 from the skin after implantation. Furthermore, the materials forming the arms may be rigid or more flexible, depending on the particular application of the sensor member and the priorities and profiles of each particular patient. In the case the arms 121 are flexible, the flexibility of the arms 121 may help facilitate easier insertion, since the arms can be urged upwardly and inwardly against the center of the sensor member 12 during insertion, and then may flare outwards and lodge in the dermis when the sensor member is pulled back, to make it more difficult to remove the sensor member 12 from the skin.

FIG. 13 shows the distal end of the sensor member 12 from FIG. 12A in greater detail. In the embodiment shown, the sensor member 12 is a flat ribbon or otherwise planar shape, and includes arms 121 at its distal end that are angled back towards a proximal end of the sensor member 12, for example, in an arrowhead-type shape, or more generally forming an angle $\gamma$. A distal end of the sensor member 12 is rounded in this embodiment, and may be deployed together with a sharp inserter. In other embodiments, the distal tip of the sensor member itself may be sharp. As can be seen, the angle $\gamma$ formed by the tip is such that the sensor member may be easily implanted into a patient's skin, and may flare radially outwardly into arms 121. The arms 121 may have a trailing edge that forms an angle $\theta$ that is greater than the angle $\gamma$ formed by the tip. A greatest width w of the portion of the sensor member at the arms 121 is further selected so as to facilitate a stronger engagement with the surrounding tissue after implantation. In some embodiments, the width w of the sensor member at the arms may be, for example, 500 µm, and/or may be approximately 40% wider than the width of the rest of the sensor member, in order to adequately engage the surrounding tissue. In other embodiments, the width of the sensor member at the arms may instead be larger or smaller, depending on for example, the amount or strength of anchoring desired.

Other variations may also be contemplated. For example, the arms may not be limited to placement at the free end of the sensor member, and instead, may protrude away from the central region of the sensor member at a more proximal location. To that effect, the corresponding positioning of the analyte sensing region relative to the arms may also vary, whether the analyte sensing region is placed more distal, at a same axial position as, or more proximal to the arms. In some embodiments, the ends of the arms may be flared outward to increase engagement. In other embodiments, more or less than two arms may be formed, for example, four arms, a T-shaped profile, or a circumferential cone or umbrella profiled shape, or a portion thereof, may be formed by the anchoring feature. To this effect, the lateral extensions may be any shape, size, angle, and/or have any placement on the sensor member, so long as they serve to increase anchoring of the sensor member in the skin after implantation. Furthermore, with this embodiment, as with the previous embodiments and embodiments described hereafter, the sensor member body has been described as being substantially flat for simplicity. However, in an alternative arrangement, the sensor member body may instead be, for example, cylindrical or have a square or rectangular or any other polygonal cross-section, either entirely or only in portions thereof, based on the specific design of each sensor member. For example, in embodiments where the distal tip is a circumferential cone, the body may further be cylindrical in shape, at least in regions that connect to the distal tip.

FIG. 12B is similar to FIG. 12A, in that two arms 121' are formed at or near the distal free end or tip of the sensor member 12', while the analyte sensing region 120' is positioned more proximally on the sensor member 12' so as to be positioned in the dermis upon implantation. To this effect, the sensor member 12' shown in FIG. 12B is similar in length and in the positioning of the sensing region as compared to the previous sensor members shown in FIG. 3B and FIG. 7B, where the additional length of the sensor member 12' allows for more secure anchoring of the sensor member as a whole deeper in the hypodermis of the patient's skin. The various modifications discussed with respect to the sensor member 12 in FIG. 12A can also be translated similarly to vary the embodiments possible with the arrangement shown in FIG. 12B. Furthermore, in some cases, either an additional anchoring means may be positioned more proximally on the sensor member 12', for example, in the dermis, in addition to or in lieu of the arms 121' shown in FIG. 12B. In such cases, the extension of the sensor member 12' into the hypodermis may work together with a more proximally positioned anchoring portion 121' to more securely hold the sensor member 12' in the patient's skin after implantation.

Figure 14:
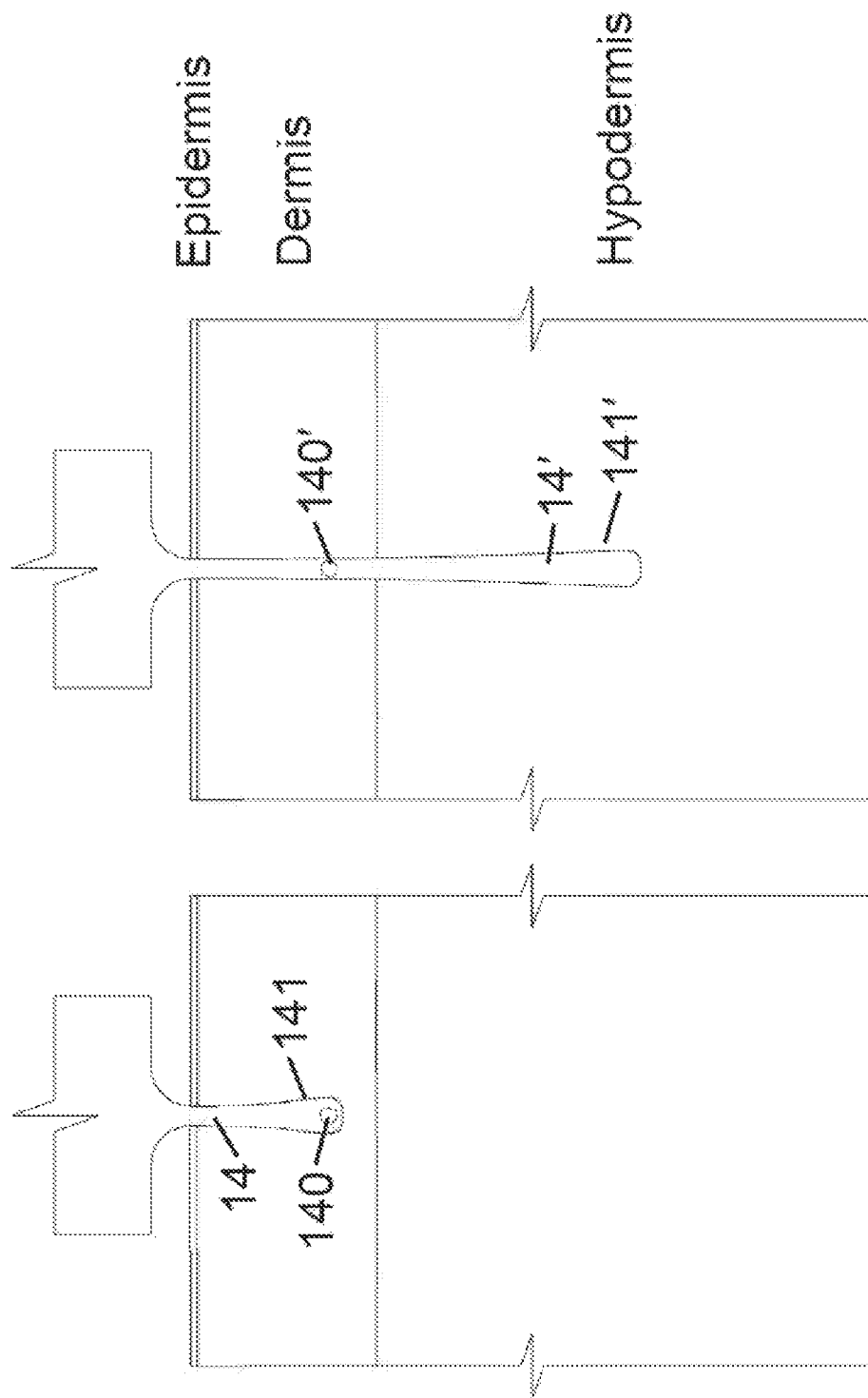
FIGS. 14A and 14B schematically illustrate analyte sensors with various lengths according to a fifth embodiment of the invention.
Figure 15:
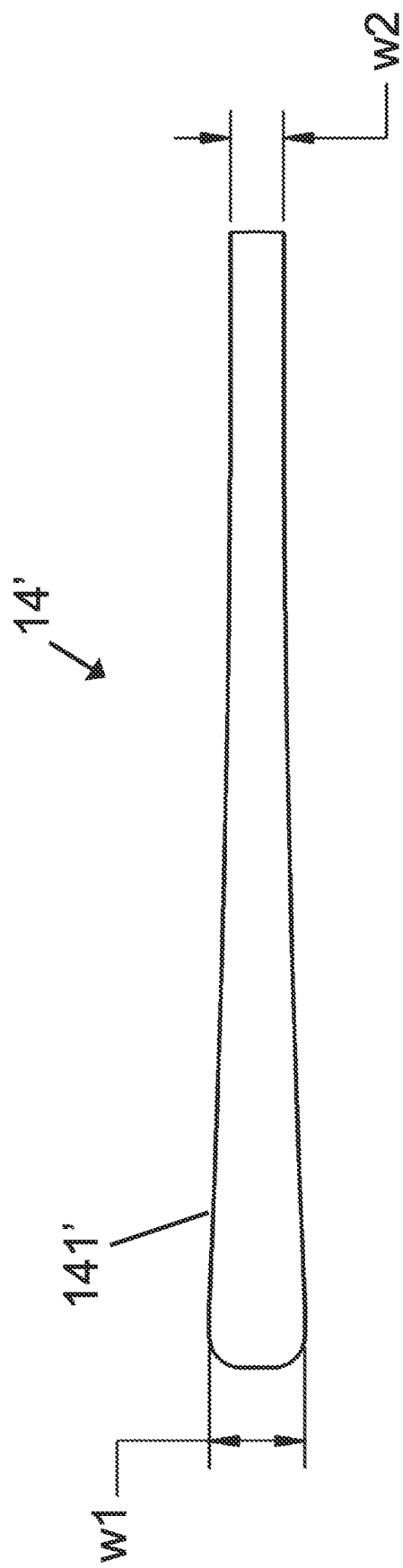
FIG. 15 shows a side view of an end of the analyte sensor in FIGS. 14A and/or 14B.

FIGS. 14A to 15 show still further sensor members according to a fifth embodiment of the invention. The embodiment in FIGS. 14A to 15 do not include a variable surface feature that is intended to catch against surrounding tissue after the sensor member is implanted. Rather, the sensor members 14, 14' in FIGS. 14A to 15 include a distal region that gradually increases in size as the sensor member extends distally, in order to form an enlarged wedge shape 141, 141' at a distal end thereof. The wedged region 141, 141' will more naturally engage the surrounding tissue in a stronger manner while potentially minimizing irritation of the surrounding tissue. While the embodiment shown in FIGS. 14A to 15 may not form as strong an anchoring means as some of the previously described embodiments, the embodiment will have a stronger anchoring means than, for example, the embodiment shown in FIG. 2. Different anchoring means with a wide variety of anchoring strengths can provide flexibility for different situations, for example, different anchors may be selected for patients with more or less delicate skin, for placement at different places on the body, and/or for people with more or less active lifestyles, among other factors.

FIG. 15 shows an enlarged view of a distal region of the sensor member 14'. As seen in FIG. 15, the sensor member 14' is simple in design and may also potentially be easier and more inexpensive to manufacture. A distal end 141' has a width w1 that is wider than a more proximal region of the sensor member body that has a width w2, for example, by about 40%. In various other embodiments, the enlarged region at the distal end may alternatively be arranged such that the width w1 is greater than the width w2 of the more proximal region by different amounts or ratios. Here, also as similarly discussed in previous embodiments, it may further be advantageous for the sensor member to be, for example, cylindrical and/or conically shaped, rather than flat, although flat arrangements may also work well and may be easier to manufacture.

Referring back to FIGS. 14A and 14B, FIG. 14A again shows a shorter sensor member which only extends into the dermis of the patient when fully inserted. The analyte sensing region 140 may be positioned at or near a distal tip of the sensor member to ensure sufficient advancement into the patient's skin, or in other embodiments, may be more proximally located. Meanwhile, the sensor member 14' in FIG. 14B is longer, and extends into the patient's hypodermis or subcutaneous layer, while the analyte sensing region 140' remains positioned more proximally in the patient's dermis even when the sensor member 14' is fully inserted. The wedge region 141' may begin flaring outward or widen in the hypodermis region, or may start increasing in width more proximally in the dermis to a maximum width in the hypodermis. Other arrangements are also possible.

Figure 16:
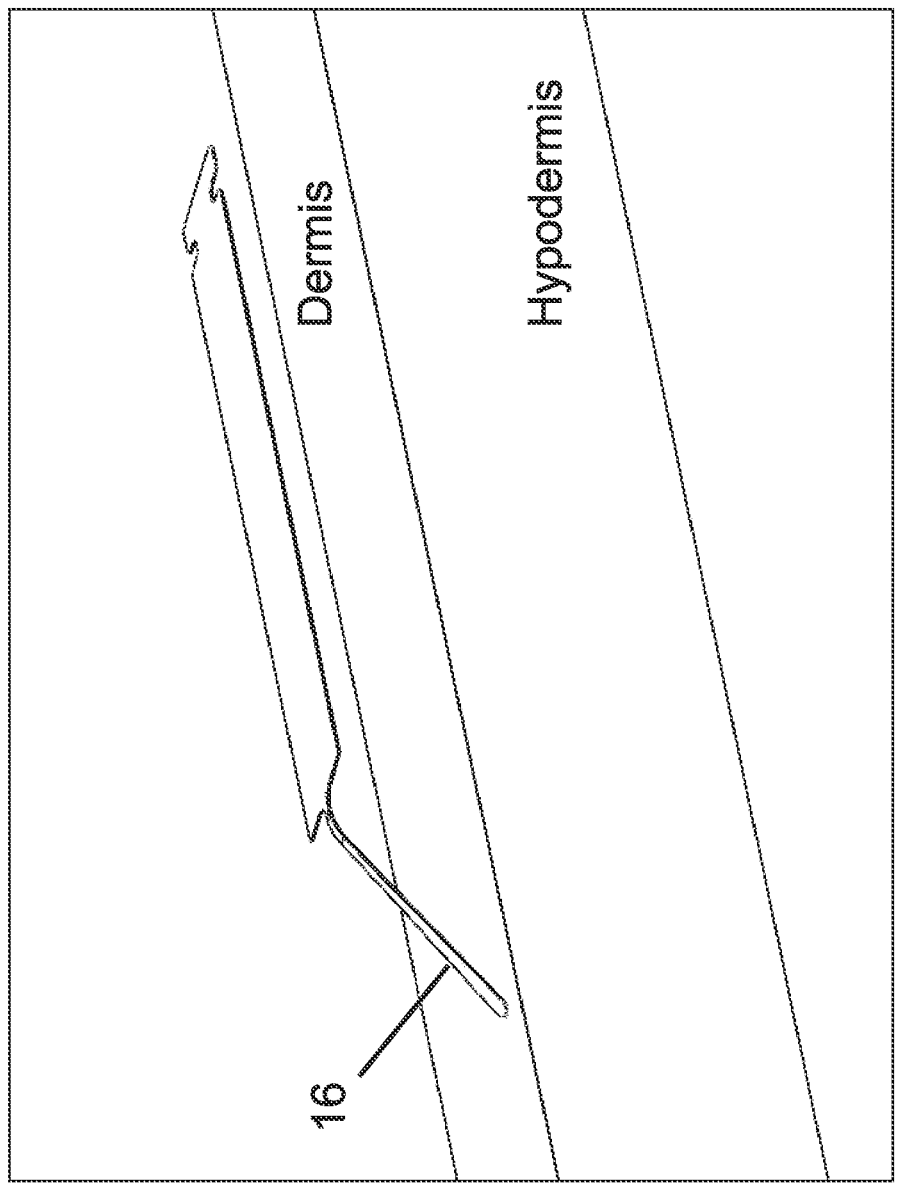
FIG. 16 schematically shows an insertion angle of an analyte sensor that extends into a patient's dermis according to some embodiments of the invention.
Figure 17:
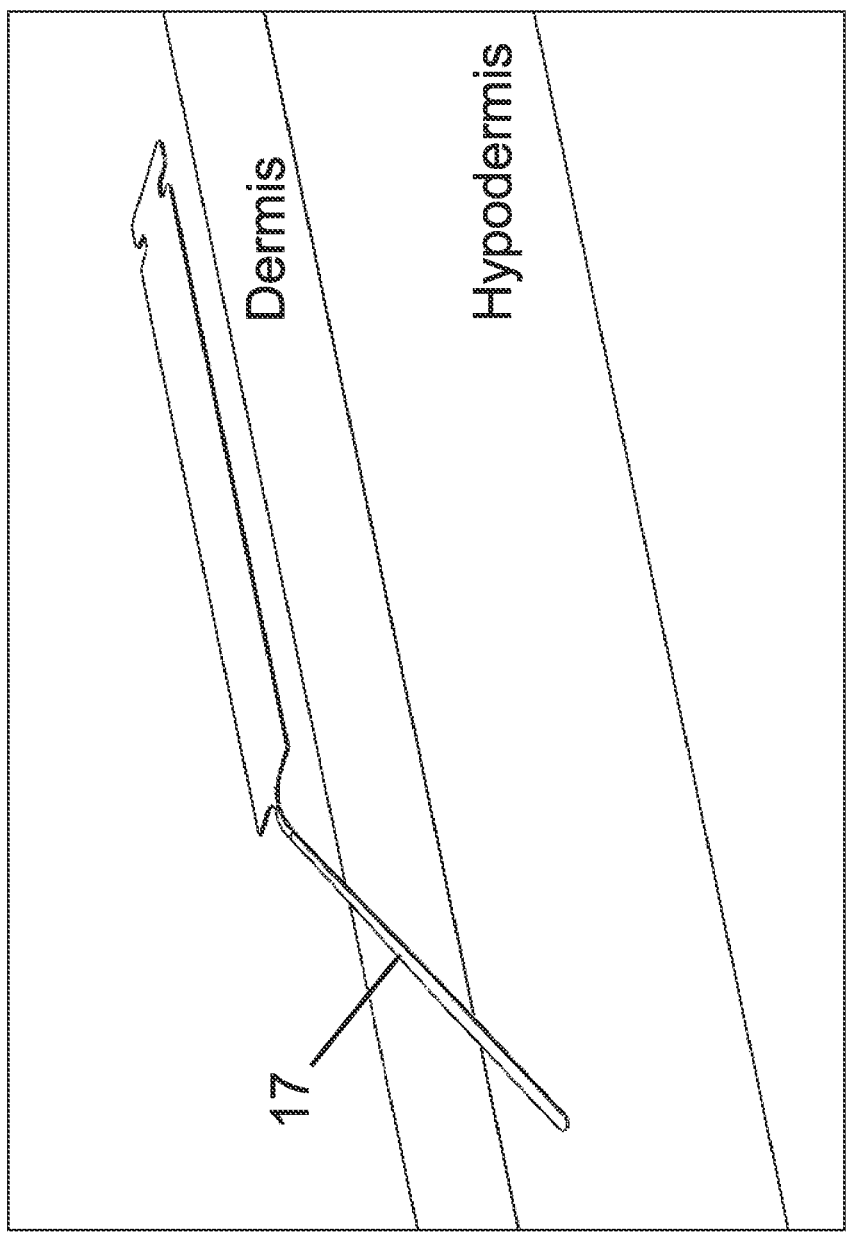
FIG. 17 schematically shows an insertion angle of an analyte sensor that extends into a patient's hypodermis according to some embodiments of the invention.

As previously discussed, an insertion angle of sensor members according to different embodiments of the invention may also vary. For simplicity, the embodiments in FIGS. 1 to 15 have been described generally where an insertion angle is perpendicular to a surface of the patient's skin, while the embodiments of monitors in FIGS. 19 to 22 show sensor members that are advanced into the patient's skin at an acute angle rather than a perpendicular angle. Exemplary sensors are schematically shown in FIGS. 16 and 17 to illustrate further example sensor arrangements that can be utilized with the various embodiments of the invention. The housings of the monitors in FIGS. 16 and 17 have been omitted in order to see the sensor members more clearly in isolation. First, in FIG. 16, sensor member 16 extends at an angle to a body of the sensor member which may house, for example, electrical contacts or other circuitry that interacts with other parts of the monitor. The sensor member 16 has been inserted at an angle to the skin of the patient, and only extends into the patient's dermis. Such angle may be, for example, approximately 30° relative to the surface of the patient's skin. Other angles of insertion are also contemplated, for example, about 45° relative to the surface of the patient's skin, or 90° relative to the surface of the patient's skin as previously discussed. However, in still other embodiments, any angle between 0° and 90°, or any angle up to 45°, or for example, more specifically between 30° and 45°, can be selected based on various factors associated with the device, patient, and/or other parameters. Meanwhile, in FIG. 17, the sensor member 17 is similarly arranged to the sensor member 16 in FIG. 16, but is longer and extends into the hypodermis of the patient's skin. Here, most notably, while not shown, the analyte sensing region will still be configured to be positioned within the dermis of the patient's skin, consistent with the embodiments described above.

In addition to the embodiments that have already been described above, it is also possible to combine embodiments, e.g., different features from the various described embodiments, to provide even more different variations of sensor members, without departing from the spirit or scope of the invention. For example, the sawtooth anchors in FIGS. 7A to 11 may further be formed with a widening wedge shape similarly as discussed with respect to the sensor members in FIGS. 14A to 15, in order to increase the engagement of the sawtooth surface features with the surrounding tissue. Other variation of surface features or larger anchoring features may also be contemplated, without departing from the spirit or scope of the invention, so long as the placement of the analyte sensing region is in the dermis upon implantation, and some sort of additional anchoring means is utilized, whether by increased length into the hypodermis and/or additional surface features.

Different ways of introducing the various sensor members described above may also be included within the spirit and scope of the invention. For example, in the discussion of the embodiment in FIGS. 12A to 13 above, it is contemplated that embodiments of the sensor member with a sharp distal tip may be able to pierce the skin itself during insertion. However, in a majority of cases, the distal end of the sensor member may not be able to pierce the skin itself, and deployment may depend on, for example, a separate needle or other introducer in which the sensor member is housed. Such embodiments may involve advancing the introducer, which may include a sharp tip, into the skin with the sensor member housed therein, and then retracting the introducer while holding the sensor member in place, so that the sensor member remains under the patient's skin after the introducer has been fully removed. In such embodiments, while a width of a proximal region of the sensor member may be narrower than a slot in the introducer to facilitate holding of a majority of the sensor member in the introducer, at least part of the sensor member, for example, distal regions that may be widened, may have a resting width that is greater than the width of the slot in the introducer, such that at least part of the distal end of the sensor member may be flexed inwardly by the introducer. Here, when the introducer is retracted after advancement into the patient's skin, the distal end of the sensor member may resiliently widen again to increase engagement with the surrounding tissue. The radial constraining of the sensor member during implantation may also help advance the sensor member into the skin, for example, less abrasively than if the sensor member and introducer were wider or had a larger footprint.

The structure/material of the portion of the sensor member that extends into and/or through the dermis may include without limitation, biocompatible material that is non-smooth, and particularly includes an architecture that aids tissue ingrowth in order to facilitate anchoring of the material into the dermis and/or hypodermis/subcutaneous layer. Examples of these materials include polyester, polypropylene cloth, polytetrafluoroethylene felts, expanded polytetrafluoroethylene, and porous silicone.

In addition, the invention should not be limited to the structures and/or shapes described in the embodiments above. Structures/shapes that support an anchoring mechanism may include, without limitation, mechanical mechanisms (e.g., prongs, spines, barbs, wings, hooks, helical surface topography, gradually changing diameter, and/or the like), which aids in immobilizing the sensor member in the dermis and/or hypodermis/subcutaneous layer.

The term "biocompatible," as used herein, is used in its ordinary sense, including, without limitation, compatibility with living tissue or a living system by not being toxic. The biocompatible material may be polymeric or metallic. Suitable polymeric materials may be selected from natural or synthetic polymers preferably selected from the group comprising, but not limited to, the following: polyglycolic acid (PGA), polylactic acid (PLA), polyethylene (PE), polypropylene (PP), polyimide (PI), polyethylene terephthalate (PET), polymethyl methacrylate (PMMA), polytetrafluoroethylene (PTFE), polyurethanes (PURs), polyvinyl chloride (PVC), silicones or mixtures of these. Suitable metallic materials may be selected from the group including, but not limited to, the following: titanium and its alloys, steels, cobalt and its alloys.

In one or more embodiments, the sensor member structure/material is "non-adhesive to tissue". This term, "non-adhesive to tissue," as used herein, is used in its ordinary sense, including, without limitation, a material or surface of a material to which cells and/or cell processes may adhere poorly at the molecular level, and/or to which cells and/or cell processes may adhere poorly to the surface of the material.

The sensor member structure material may be prepared according to any of the methods known in the art as suitable for processing the aforementioned plastic or metal materials, for example, by means of injection molding, compression molding, casting molding, 3D molding, die casting techniques, spin casting, laser cutting, stamping, lithographic techniques, thermoforming, or other processes for forming small plastic and/or metal objects for medical use.

The anchoring system according to one or more embodiments has the advantage of allowing the anchoring of the sensor member in a stable and safe way, without having to resort to adhesives or sutures. For example, in the case of continuous glucose monitors, the anchoring assembly allows the sensor member to be kept in position for the entire duration of the glucose concentration monitoring period, without the need to replace the sensor member. In addition, the anchoring system of this disclosure, because of its simple use, does not require the intervention of specialized medical personnel and may therefore be applied or removed by the subject.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present disclosure, and should not be interpreted in an idealized or overly formal sense, unless expressly so defined herein.

While the subject matter of the present disclosure has been described in connection with certain embodiments, it is to be understood that the subject matter of the present disclosure is not limited to the disclosed embodiments, but, on the contrary, the present disclosure is intended to cover various modifications and equivalent arrangements included within the spirit and scope of the appended claims, and equivalents thereof.

What is claimed is:

1. A system comprising:
a monitor for determining analyte concentrations in vivo, comprising:
a housing configured to adhere to the skin of a subject;
an elongate and monolithic sensor body configured to extend from the housing into the skin of the subject, wherein a distal end of the sensor body is devoid of any sharp tip, and wherein the sensor body comprises at least one engagement surface configured to facilitate increased anchoring of the sensor body in the skin of the subject, the at least one engagement surface extending laterally away from a central axis of the sensor body by a greater distance than another region of the sensor body that is closer to the housing extends away from the central axis; and an analyte sensing region positioned on the sensor body such that the analyte sensing region is configured to be held in the dermis of the skin of the subject;

a separate introducer comprising a tip and defining a slot, wherein the tip of the introducer is configured to pierce the skin of the subject while the sensor body is housed in the slot for inserting the sensor body into the skin of the subject, and wherein the introducer is removable from the skin of the subject while the sensor body remains inserted in the skin of the subject; and wherein an inner width of the slot of the introducer is less than a maximum width of the at least one engagement surface of the sensor body measured in a direction perpendicular to the central axis, such that the at least one engagement surface is radially constrained by the slot and configured to flex inwardly when held in the slot.

2. The system of claim 1, wherein the monitor is a glucose monitor configured to determine glucose concentrations in vivo.

3. The system of claim 1, wherein the at least one engagement surface extends at least partially radially away from other portions of the sensor body.

4. The system of claim 3, wherein the at least one engagement surface forms at least one barb element on an outer surface of the sensor body.

5. The system of claim 3, wherein the at least one engagement surface forms at least one arm that extends at least partially radially away from the other portions of the sensor body.

6. The system of claim 3, wherein the at least one engagement surface forms a wedge that increases in width as the engagement surface extends towards the distal end of the sensor body.

7. The system of claim 3, wherein the at least one engagement surface facilitates a unidirectional insertion of the sensor body into the skin of the subject, while restricting removal of the sensor body from the skin of the subject after insertion.

8. The system of claim 1, wherein the sensor body is of a sufficient length to extend into the hypodermis of the subject without the analyte sensing region extending into the hypodermis.

9. The system of claim 1, wherein the sensor body is configured to be arranged at an acute angle relative to a bottom surface of the housing so as to extend into the skin of the subject at substantially the same angle.

10. The system of claim 1, wherein the sensor body extends substantially in a first plane, and wherein the at least one engagement surface extends laterally away from the first plane.

11. The system of claim 1, wherein the sensor body extends from a proximal end adjacent to a bottom surface of the housing to the distal end and has a length measured between the proximal and distal ends, and wherein a width of the sensor body continuously increases over a majority of the length of the sensor body as the sensor body extends towards the distal end.

12. The system of claim 1, wherein the sensor body extends from a proximal end adjacent to a bottom surface of the housing to the distal end and has a length measured between the proximal and distal ends, wherein a width of the sensor body continuously increases over a first portion of the length to a greatest width of the sensor body as the sensor body extends towards the distal end, and wherein the first portion of the length is longer than a second portion of the length measured between the greatest width of the sensor body and the distal end of the sensor body.

13. A method of determining analyte concentrations in vivo in a subject using a monitor comprising a housing configured to adhere to the skin of the subject, an elongate and monolithic sensor body configured to extend from the housing into the skin of the subject, wherein a distal end of the sensor body is devoid of any sharp tip, and wherein the sensor body comprises at least one engagement surface configured to facilitate increased anchoring of the sensor body in the skin of the subject, the at least one engagement surface extending laterally away from a central axis of the sensor body by a greater distance than another region of the sensor body that is closer to the housing extends away from the central axis, and an analyte sensing region positioned on the sensor body, the method comprising:

piercing the skin of the subject with a tip of a separate introducer while the sensor body is housed in a slot defined by the introducer to insert the sensor body into the skin of the subject, wherein an inner width of the slot of the introducer is less than a maximum width of the at least one engagement surface of the sensor body measured in a direction perpendicular to the central axis, such that the at least one engagement surface is radially constrained by the slot and configured to flex inwardly when held in the slot;

removing the introducer from the skin of the subject while the sensor body remains inserted in the skin of the subject, such that the sensor body extends from the housing into the skin of the subject, the analyte sensing region is held in the dermis of the skin of the subject, and the engagement surface engages the surrounding tissue to increase the anchoring of the sensor body in the skin of the subject;

detecting a signal associated with the analyte in the subject; and determining a concentration of the analyte in the subject from the signal.

14. The method of claim 13, wherein the monitor comprises a glucose monitor configured to determine a concentration of glucose in the subject.

15. The method of claim 13, wherein the sensor body is configured to extend into the skin of the subject at an acute angle relative to the surface of the skin of the subject.

16. The method of claim 13, wherein the at least one engagement surface extends at least partially radially away from other portions of the sensor body.

17. The method of claim 13, wherein the sensor body is of a sufficient length to extend into the hypodermis of the subject without the analyte sensing region extending into the hypodermis.

* * * * *